United States Patent
Osterholm

(10) Patent No.: US 12,359,324 B2
(45) Date of Patent: *Jul. 15, 2025

(54) SYSTEM FOR STERILIZING EQUIPMENT, ASSOCIATED METHOD, AND CHLORINE DIOXIDE GAS GENERATING DEVICE FOR USE WITH SAME

(71) Applicant: CUPOD LLC, Hermitage, PA (US)

(72) Inventor: Wayne Osterholm, New Wilmington, PA (US)

(73) Assignee: CUPOD LLC, Hermitage, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/915,728

(22) Filed: Oct. 15, 2024

(65) Prior Publication Data

US 2025/0059654 A1 Feb. 20, 2025

Related U.S. Application Data

(63) Continuation-in-part of application No. 18/411,478, filed on Jan. 12, 2024, now Pat. No. 12,146,230, (Continued)

(51) Int. Cl.
*C25B 1/26* (2006.01)
*A61L 2/20* (2006.01)
(Continued)

(52) U.S. Cl.
CPC ...... *C25B 1/26* (2013.01); *A61L 2/20* (2013.01); *A61L 2/24* (2013.01); *B65B 55/18* (2013.01); (Continued)

(58) Field of Classification Search
CPC ....................................................... A61L 2/20
See application file for complete search history.

(56) References Cited

U.S. PATENT DOCUMENTS 3,716,961 A * 2/1973 Cope .................. B65B 55/02
422/294
4,002,186 A 1/1977 Fink
(Continued)

FOREIGN PATENT DOCUMENTS

CN 213387806 U 6/2021
JP 08309099 A * 11/1996 ............. D06F 58/14
(Continued)

OTHER PUBLICATIONS

Translation of abstract of JP 08-309099 A (Year: 1996).*
(Continued)

*Primary Examiner* — Harry D Wilkins, III
(74) *Attorney, Agent, or Firm* — The Powers IP Law Firm

(57) ABSTRACT

A chlorine dioxide gas generating system for sterilizing equipment in a chamber is provided. The system includes a chlorine dioxide gas generating device configured to generate chlorine dioxide gas, a vacuum pump, and a port assembly comprising a port member fluidly coupled to the vacuum pump and configured to be maintained in an interior of the chamber. The vacuum pump is configured to pump the chlorine dioxide gas from the device into the chamber through the port member in order to sterilize the equipment, and after a predetermined period of time, pull a gas other than the chlorine dioxide gas into and out of the chamber at least one time through the port member in order to remove humidity from the chamber and cause the chlorine dioxide gas to be drawn out of the chamber through the port member.

28 Claims, 33 Drawing Sheets

Related U.S. Application Data which is a continuation-in-part of application No. 18/126,640, filed on Mar. 27, 2023, now Pat. No. 11,905,606.

(60) Provisional application No. 63/324,252, filed on Mar. 28, 2022.

(51) Int. Cl.
| | | |
|---|---|---|
| *A61L 2/24* | (2006.01) | |
| *A61L 101/06* | (2006.01) | |
| *B65B 51/14* | (2006.01) | |
| *B65B 55/18* | (2006.01) | |
| *C25B 9/19* | (2021.01) | |
| *C25B 9/60* | (2021.01) | |
| *C25B 15/08* | (2006.01) | |

(52) U.S. Cl.
CPC .................. *C25B 9/19* (2021.01); *C25B 9/60* (2021.01); *C25B 15/083* (2021.01); *A61L 2101/06* (2020.08); *A61L 2202/11* (2013.01); *A61L 2202/15* (2013.01); *A61L 2202/181* (2013.01); *B65B 51/146* (2013.01)

(56) References Cited

U.S. PATENT DOCUMENTS

| | | | |
|---|---|---|---|
| 4,176,032 A | 11/1979 | Stevenson, Jr. | |
| 4,178,224 A | 12/1979 | Porter | |
| 4,441,965 A | 4/1984 | Matsumura | |
| 4,683,039 A | 7/1987 | Twardowski et al. | |
| 4,941,308 A * | 7/1990 | Grabenkort | A61M 25/002 |
| | | | 53/445 |
| 5,597,019 A | 1/1997 | Thomas et al. | |
| 5,932,085 A | 8/1999 | Cowley et al. | |
| 5,965,004 A | 10/1999 | Cowley et al. | |
| 6,235,240 B1 * | 5/2001 | Heredia | A61L 2/20 |
| | | | 422/31 |
| 6,602,466 B2 | 8/2003 | Hamilton et al. | |
| 12,146,230 B2 * | 11/2024 | Osterholm | C25B 15/083 |
| 2001/0038805 A1 | 11/2001 | Hamilton | |
| 2002/0185423 A1 | 12/2002 | Boyd | |
| 2004/0211676 A1 | 10/2004 | Herrington | |
| 2004/0213698 A1 | 10/2004 | Tennakoon et al. | |
| 2006/0120928 A1 * | 6/2006 | Annacone | B01J 3/03 |
| | | | 422/105 |
| 2007/0084144 A1 * | 4/2007 | Labrecque | A61B 50/30 |
| | | | 422/26 |
| 2009/0217626 A1 * | 9/2009 | Kemp | A61L 2/24 |
| | | | 53/97 |
| 2010/0189631 A1 | 7/2010 | Noszticzius et al. | |
| 2010/0310418 A1 * | 12/2010 | Mason | A61L 2/20 |
| | | | 422/37 |
| 2011/0044853 A1 * | 2/2011 | Devine | A61L 2/28 |
| | | | 422/36 |
| 2011/0135537 A1 * | 6/2011 | Schwartz | A61L 2/26 |
| | | | 422/292 |
| 2012/0012466 A1 | 1/2012 | Sperry | |
| 2016/0193375 A1 * | 7/2016 | Laflamme | A61L 2/208 |
| | | | 422/108 |
| 2017/0253980 A1 | 9/2017 | Matsubara | |
| 2023/0304168 A1 * | 9/2023 | Osterholm | C01B 11/022 |
| 2024/0141511 A1 * | 5/2024 | Osterholm | C25B 15/083 |

FOREIGN PATENT DOCUMENTS

| | | | | |
|---|---|---|---|---|
| JP | 2005027753 A | * | 2/2005 | ............... A61L 2/20 |
| WO | 2001060750 A2 | | 8/2001 | |
| WO | WO-2011070329 A1 | * | 6/2011 | ............ A61B 50/30 |
| WO | 2013070096 A1 | | 5/2013 | |

OTHER PUBLICATIONS

Machine translation of JP 2005-027753 A (Year: 2005).*
McDonald et al, Fabrication of microfluidic systems in poly(dimethylsiloxane), Electrophoresis, vol. 21, No. 1, Jan. 2000, pp. 27-40 (Year: 2000) [14 pages total].
Zhu et al, Preparation and Evaluation of Novel Solid Chlorine Dioxide-based Disinfectant Powder in Single-pack, Biomedical and Environmental Sciences, vol. 21, No. 2, Feb. 2008, pp. 157-162 (Year: 2008) [6 pages total].
International Search Report; PCT/US2024/011498 (Issued Jun. 24, 2024) [5 pages total].
Written Opinion of the International Searching Authority; PCT/US2024/011498 (Issued Jun. 24, 2024) [10 pages total].

* cited by examiner

SYSTEM FOR STERILIZING EQUIPMENT, ASSOCIATED METHOD, AND CHLORINE DIOXIDE GAS GENERATING DEVICE FOR USE WITH SAME

CROSS-REFERENCE TO RELATED APPLICATIONS

This application claims priority to and claims the benefit of U.S. patent application Ser. No. 18/411,478, filed Jan. 12, 2024, which claims priority to and claims the benefit of U.S. patent application Ser. No. 18/126,640, filed Mar. 27, 2023, which claims priority to and claims the benefit of U.S. Provisional Patent Application Ser. No. 63/324,252, filed on Mar. 28, 2022.

TECHNICAL FIELD

This patent specification relates to the field of the generation of sanitizing substances. More specifically, this patent specification relates to devices and systems for generating chlorine dioxide gas.

BACKGROUND

Sanitizing substances and processes using sanitizing substances are in constant need. One particularly useful sanitizing substance is Chlorine dioxide gas. Chlorine dioxide gas is unstable and cannot be liquefied or compressed and therefore must be produced on-site for use. Chlorine dioxide on site production is typically generated through an acid-based method by mixing starting materials, such as sodium chlorite and hydrochloric acid, or sodium chlorite and ferric trichloride, or sodium chlorite and chlorine gas. However, these reactants, and methods utilizing them, are expensive and used for large scale production for cost effectiveness and contain impurities that need further filtration for quality and use. Because of the difficulties in generating, transporting, and storing chlorine dioxide gas, the benefits of its use are limited.

Therefore, a need exists for novel chlorine dioxide generating devices and systems. A further need exists for novel devices and systems for chlorine dioxide gas generation that produce highly pure chlorine dioxide gas on demand in a safe and cost-effective manner for personal, business and industrial sanitizing applications.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

DETAILED DESCRIPTION

Overview

Figure 1:
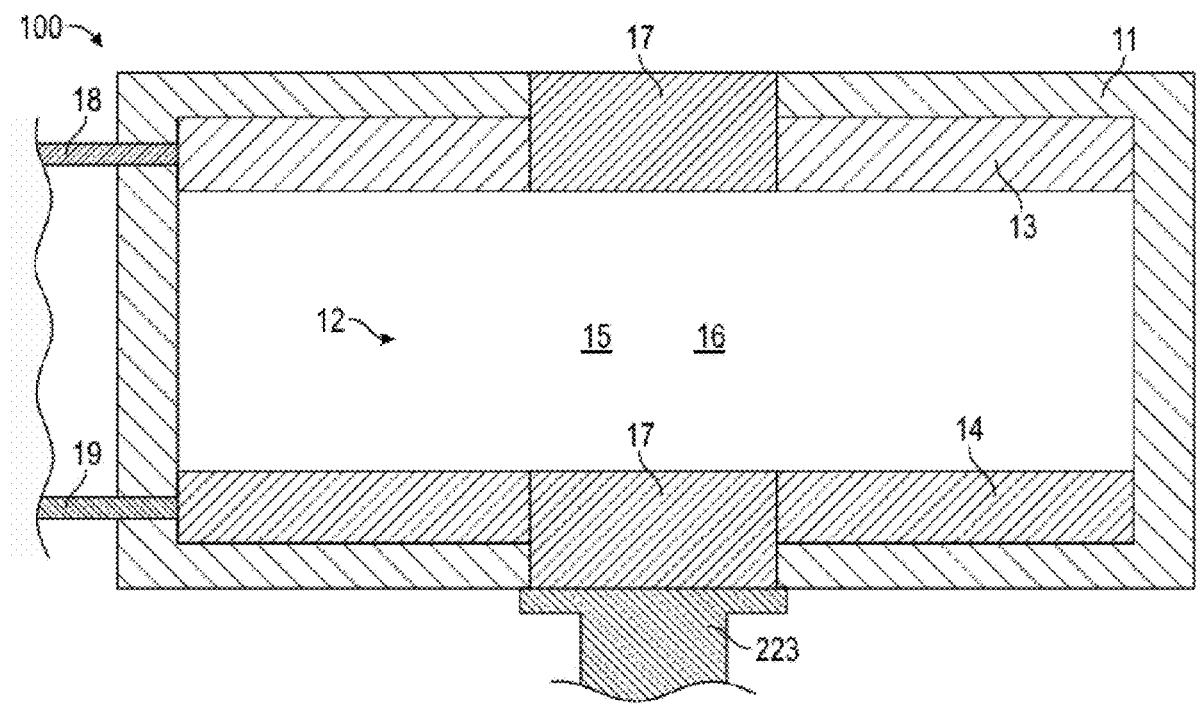
FIG. 1 depicts a sectional view of an example of a chlorine dioxide generating device according to various embodiments described herein.

A chlorine dioxide generating device and system is provided. Preferably, this device and system may utilize a combination of with water (e.g., Type I Ultra-Pure Water) and ACS reagent grade sodium chlorite for chlorine gas generation produces a highly pure, cost effective production, on demand for personal, business and industrial use. By producing controllable on site, on demand, and highly pure chlorine dioxide gas, the device enables a safe production and use of chlorine dioxide gas.

According to one aspect consistent with the principles of the invention, a chlorine dioxide generating device is provided. In some embodiments, the device may include a housing, and the housing may include a cavity. An anode and a cathode may be positioned in and coupled to the cavity so that the anode and cathode are not in contact with each other. A first reagent and a second reagent may be disposed in the cavity so that the first reagent and second reagent each contact both the anode and cathode. The first reagent may comprise water and the second reagent may comprise sodium chlorite which may be mixed to form a solution. By applying electrical current to the device so that the electrical current flows from the anode to the cathode, chlorine dioxide gas may be generated in the cavity via electrolysis. That is, the first and second reagents are configured to generate chlorine dioxide gas via electrolysis responsive to an electric current being passed into the anode and the cathode. In this manner, the anode and the cathode function as a catalyst to facilitate the generation of chlorine dioxide gas. Additionally, the device may include one or more hydrophobic membranes coupled to the housing of the chlorine dioxide generating device, which may enable the chlorine dioxide gas to exit the cavity and housing while keeping the reagents within the cavity (e.g., while preventing fluids from flowing therethrough).

In further embodiments, the device may include a proton exchange membrane which may be positioned in the cavity so that the cathode and anode may be separated by the proton exchange membrane so that the reassurance of separating the chlorine dioxide gas from other impurities is established.

According to another aspect, a chlorine dioxide generating system is provided which may utilize one or more devices to generate chlorine dioxide gas and to deposit the chlorine dioxide gas in a dispensing container to facilitate the use of the chlorine dioxide gas for cleaning, disinfecting, and other purposes. In some embodiments, the system may comprise a chlorine dioxide generating device which may be configured to generate chlorine dioxide gas via electrolysis. A dispensing container may be in communication with the device so that the chlorine dioxide gas may enter a dispensing cavity of the dispensing container. The dispensing cavity may include a liquid, such as water, which the chlorine dioxide gas may be infused or dissolved into. The system may include an activator which may supply electricity to the device to enable electrolysis.

In further embodiments, the system may comprise a dispensing container having a dispensing hydrophobic membrane which may be placed on a device so that the chlorine dioxide gas may pass through a hydrophobic membrane of the device and into the dispensing cavity via the dispensing hydrophobic membrane. Furthermore, the chlorine dioxide gas may be configured to pass directly from the chlorine dioxide gas generating device into the dispensing container without passing through intermediate components (e.g., the device may be sealingly engaged with the dispensing container). An optional vacuum pump may be in communication with the dispensing container and the device, and the vacuum pump draw excess chlorine dioxide gas out of the dispensing container and then recirculate the chlorine dioxide gas into the device and/or dispensing container so as to further concentrate the chlorine dioxide gas into the liquid within the dispensing container.

These and other advantages of the present disclosure are provided in greater detail herein.

Illustrative Embodiments

The terminology used herein is for the purpose of describing particular embodiments only and is not intended to be limiting of the invention. As used herein, the term "and/or" includes any and all combinations of one or more of the associated listed items. As used herein, the singular forms "a," "an", and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

For purposes of description herein, the terms "upper", "lower", "left", "right", "rear", "front", "side", "vertical", "horizontal", and derivatives thereof shall relate to the invention as oriented in FIG. 1. However, one will understand that the invention may assume various alternative orientations and step sequences, except where expressly specified to the contrary. Therefore, the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Although the terms "first", "second", etc. are used herein to describe various elements, these elements should not be limited by these terms. These terms are only used to distinguish one element from another element. For example, the first element may be designated as the second element, and the second element may be likewise designated as the first element without departing from the scope of the invention.

As used in this application, the term "about" or "approximately" refers to a range of values within plus or minus 10% of the specified number. Additionally, as used in this application, the term "substantially" means that the actual value is within about 10% of the actual desired value, particularly within about 5% of the actual desired value and especially within about 1% of the actual desired value of any variable, element or limit set forth herein.

A new controllable ultra-pure on-demand chlorine dioxide generating device and system are discussed herein. In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention and is not intended to limit the invention to the specific embodiments illustrated by the figures or description below.

Figure 2:
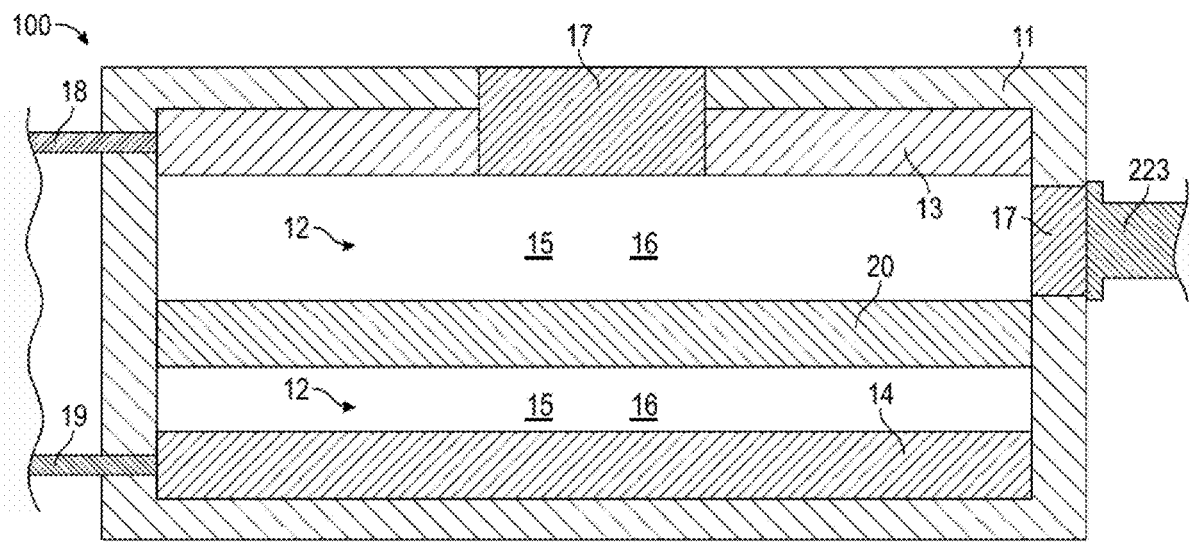
FIG. 2 illustrates a sectional view of another example of a chlorine dioxide generating device according to various embodiments described herein.
Figure 3:
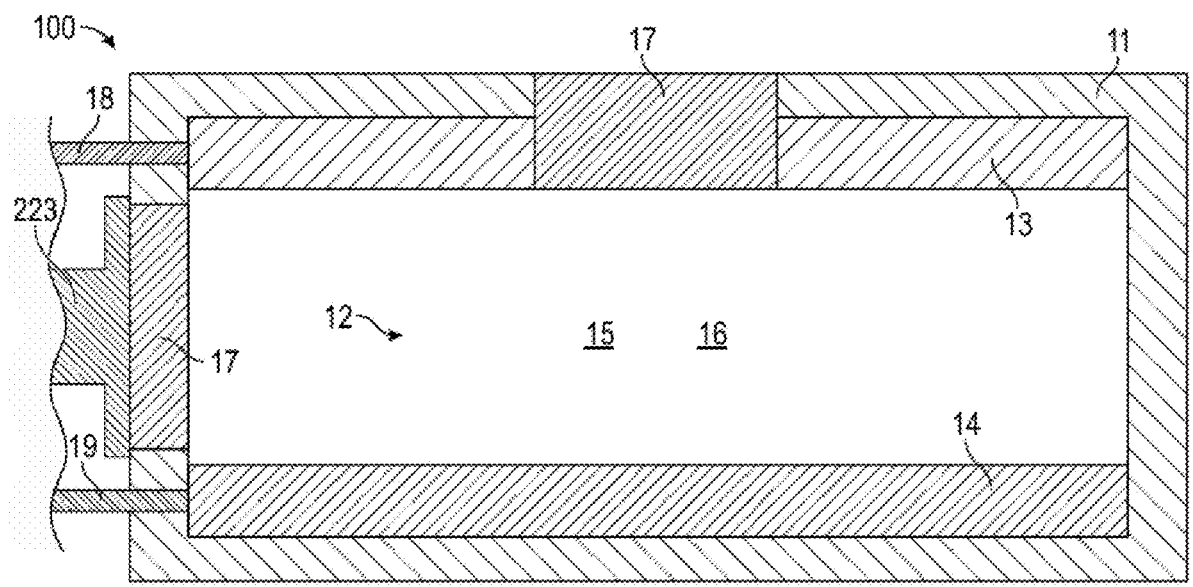
FIG. 3 shows a sectional view of yet another example of a chlorine dioxide generating device according to various embodiments described herein.

The present invention will now be described by example and through referencing the appended figures representing preferred and alternative embodiments. FIGS. 1-3 illustrate examples of a chlorine dioxide generating device ("the device") 100 according to various embodiments. The device 100 may be used to generate ultra-pure chlorine dioxide gas in a controllable and on-demand manner. In some embodiments, the device 100 may comprise a housing 11. The housing 11 may include a cavity 12. An anode 13 and a cathode 14 may be positioned in the cavity 12 so that the anode 13 and cathode 14 are not in contact with each other. A first reagent 15 and a second reagent 16 may be disposed in the cavity 12 so that the first reagent 15 and second reagent 16 each contact both the anode 13 and cathode 14. The first reagent 15 may comprise water and the second reagent 16 may comprise sodium chlorite which may be mixed to form a solution. By applying electrical current to the device 100 so that the electrical current flows from the anode 13 to the cathode 14, chlorine dioxide gas may be generated in the cavity 12 via electrolysis. The device 100 may include one or more hydrophobic membranes which may enable the chlorine dioxide gas to exit the cavity 12 and housing 11 while keeping the reagents 15, 16, within the cavity 12.

The device 100 may comprise a housing 11 which may be configured in any shape and size. For example, a housing 11 may range in size from approximately the size of a dime to industrial sizes needed for safe on demand chlorine dioxide gas at a controlled rate. Generally, a housing 11 may form the cavity 12 may also function as a structure to which the anode 13, cathode 14, and other elements of the device 100 may be directly or indirectly coupled to. In some embodiments, a housing 11 may be configured in a generally cylindrical shape. In other embodiments, a housing 11 may be configured in a generally rectangular prism shape, a hexagonal prism shape, or any other shape, including combinations of shapes.

Preferably, a housing 11 may be made from or may comprise substantially rigid materials that are not conductive to electricity, including glass, such as borosilicate glass or Pyrex®, ceramics such as alumina, porcelain, and boron carbide, various types of hard plastics, such as polyethylene (PE), Ultra-high-molecular-weight polyethylene (UHMWPE, UHMW), polypropylene (PP) and polyvinyl chloride (PVC), polycarbonate, nylon, Poly(methyl methacrylate) (PMMA) also known as acrylic, melamine, hard rubbers, fiberglass, carbon fiber, resins, such as epoxy resin, or any other material including combinations of materials that are substantially rigid and suitable for securing and positioning a heat exchange element 112 to a seating element 111.

A cavity 12 may be formed or disposed in the housing 11, and the cavity 12 may be sized and shaped to that all or portions of the anode 13 and cathode 14 may be positioned within the cavity 12 while also being separated form each other. Additionally, the cavity 12 may be sized and shaped to accommodate desired amounts of a first reagent 15 and second reagent 16 so that the reagents 15, 16, may each contact both the anode 13 and cathode 14. In some embodiments, a cavity 12 may be configured in a generally cylindrical shape, a generally rectangular prism shape, a hexagonal prism shape, or any other shape, including combinations of shapes.

The device 100 may comprise an anode 13 and a cathode 14 which may be used to perform electrolysis on the reagents 15, 16, within the cavity 12. In preferred embodiments, an anode 13 and/or a cathode 14 may be made from or may comprise Electrolysis Platinum coated Titanium. In other embodiments, an anode 13 and/or a cathode 14 may be made from or may comprise material that may be suitable for performing electrolysis on reagents 15, 16, to generate chlorine dioxide gas. Optionally, the device 100 may comprise one or more leads, such as an anode lead 18 and/or a cathode lead 19, which may be made of or may comprise an electrically conductive material, such as copper, aluminum, brass, etc., that may be cheaper than the material used to form the anode 13 and/or cathode 14. In one example, the anode 13 and the cathode 14, and associated leads may have a minimum electrical conductivity of $5.96*10^7\sigma$, at 20 degrees C. (S/m). It will also be appreciated that the anode 13 and the cathode 14, and associated leads 18, 19 may be made of suitable materials that do not corrode in the presence of, or that are wear-resistant to, sodium chlorite, including, for example and without limitation, plutonium, titanium, gold, graphene (e.g., and also including other nano-technology based materials), and graphite, each of which may be more wear resistant to sodium chlorite than copper, aluminum, and brass. An anode lead 18 and a cathode lead 19 may be used to direct and conduct power from a power supply or power supplying device to an anode 13 and cathode 14, respectively, and may be configured in any length, gauge, size, so as to enable this function.

The device 100 may comprise one or more reagents, such as a first reagent 15 and a second reagent 16, which may undergo electrolysis in the cavity 12. The first reagent 15 may comprise water and the second reagent 16 may comprise sodium chlorite which may be mixed to form a solution. In preferred embodiments, a first reagent 15 may comprise Type I Ultra-Pure Water, as defined by the American Society for Testing and Materials, and a second reagent 16 may comprise ACS Reagent grade sodium chlorite. In further embodiments, a first reagent 15 may comprise aqueous sodium chloride or saturated saline and a second reagent 16 may comprise sodium hypochlorite.

In some embodiments, the device 100 may comprise a hydrophobic membrane 17 which may be configured to prevent water from exiting the cavity, while also allowing hydrophobic materials such as chlorine dioxide gas to pass through the hydrophobic membrane 17. A hydrophobic membrane 17 may comprise any suitable hydrophobic membrane. In preferred embodiments, a hydrophobic membrane 17 may comprise a hydrophobic membrane made by Porex, such as the Porex Virtek PTFE protection vent, PMV10L with the 7 mm OD and 3 mm ID. It should be understood that a hydrophobic membrane 17 may be configured in any size and shape depending on device 100 output requirements.

In some embodiments, a hydrophobic membrane 17 may be in fluid communication with the cavity 12 and configured to allow chlorine dioxide gas to exit the cavity 12, such as for collection of the chlorine dioxide gas in a container or vessel. In further embodiments, a hydrophobic membrane 17 may be in fluid communication with the cavity 12 and configured to allow chlorine dioxide gas to enter the cavity 12, such as to allow chlorine dioxide gas to be recirculated through the device 100 for concentrating purposes. Hydrophobic membrane(s) 17 are not required, but may be needed for the containment and production of chlorine dioxide gas, as a hydrophobic membrane 17 retains the liquid while allowing the generated chlorine dioxide gas to escape.

In some embodiments, the device 100 may comprise a proton exchange membrane (PEM) 20. In preferred embodiments, a proton exchange membrane may be positioned in the cavity 12 so that the cathode 14 and anode 13 may be separated by the proton exchange membrane 20 so that the reassurance of separating the chlorine dioxide gas from other impurities is established. In preferred embodiments, a proton exchange membrane 20 may be or may comprise a Nafion 211 Proton Exchange Membrane. PEMs can be made from either pure polymer membranes or from composite membranes, where other materials are embedded in a polymer matrix. One of the most common and commercially available PEM materials is the fluoropolymer (PFSA) Nafion, a DuPont product. While Nafion is an ionomer with a perfluorinated backbone like Teflon, there are many other structural motifs used to make ionomers for proton-exchange membranes. Many use polyaromatic polymers, while others use partially fluorinated polymers.

FIG. 1 shows an example of a device 100 according to various embodiments. In this and in some embodiments, the device 100 may comprise a cavity 12 having an anode 13 and a cathode 14 at opposite ends of the cavity 12. A first reagent 15 comprising Type I Ultra-Pure Water and a second reagent 16 comprising ACS Reagent grade sodium chlorite may be disposed in the cavity 12 to contact the anode 13 and cathode 14. The anode 13 may comprise a first hydrophobic membrane 17 and the cathode 14 may optionally comprise a second membrane 17. Electricity may be supplied to the anode 13 and cathode 14 via an anode lead 18 and a cathode lead 19, respectively, to generate chlorine dioxide gas via electrolysis of the reagents 15, 16. The chlorine dioxide gas may pass through the first hydrophobic membrane 17 to exit the device 100. In further embodiments, chlorine dioxide gas may be recirculated through the device 100 by being communicated through the second hydrophobic membrane 17 via a gas conducting conduit 223. In this manner, the second hydrophobic membrane 17 is configured to allow the chlorine dioxide gas to re-enter the cavity and be reconcentrated therein.

FIG. 2 depicts another example of a device 100 according to various embodiments. In this and in some embodiments, the device 100 may comprise a cavity 12 having an anode 13 and a cathode 14 at opposite ends of the cavity 12. A first reagent 15 comprising Type I Ultra-Pure Water and a second reagent 16 comprising ACS Reagent grade sodium chlorite may be disposed in the cavity 12 to contact the anode 13 and cathode 14. The anode 13 may comprise a first hydrophobic membrane 17 and the cathode 14 may optionally comprise a second membrane 17. A proton exchange membrane 20 may be positioned in (e.g., coupled to and located in) the cavity 12 so that the anode 13 and cathode 14 are separated by the proton exchange membrane 20 in order to ensure that the chlorine dioxide gas is separated from impurities before exiting the housing 11. Electricity may be supplied to the anode 13 and cathode 14 via an anode lead 18 and a cathode lead 19, respectively, to generate chlorine dioxide gas via electrolysis of the reagents 15, 16. The chlorine dioxide gas may pass through the first hydrophobic membrane 17 to exit the device 100. In further embodiments, chlorine dioxide gas may be recirculated through the device 100 by being communicated through the second hydrophobic membrane 17 via gas conducting conduit 223 and may then exit the device 100 via the first hydrophobic membrane 17.

FIG. 3 illustrates yet another example of a device 100 according to various embodiments. In this and in some embodiments, the device 100 may comprise a cavity 12 having an anode 13 and a cathode 14 at opposite ends of the cavity 12. A first reagent 15 comprising Type I Ultra-Pure Water and a second reagent 16 comprising ACS Reagent grade sodium chlorite may be disposed in the cavity 12 to contact the anode 13 and cathode 14. The anode 13 may comprise a first hydrophobic membrane 17 and a second membrane 17 may be disposed in the housing 11. Electricity may be supplied to the anode 13 and cathode 14 via an anode lead 18 and a cathode lead 19, respectively, to generate chlorine dioxide gas via electrolysis of the reagents 15, 16. The chlorine dioxide gas may pass through the first hydrophobic membrane 17 to exit the device 100. In further embodiments, chlorine dioxide gas may be recirculated through the device 100 by being communicated through the second hydrophobic membrane 17 via gas conducting conduit 223.

Figure 4:
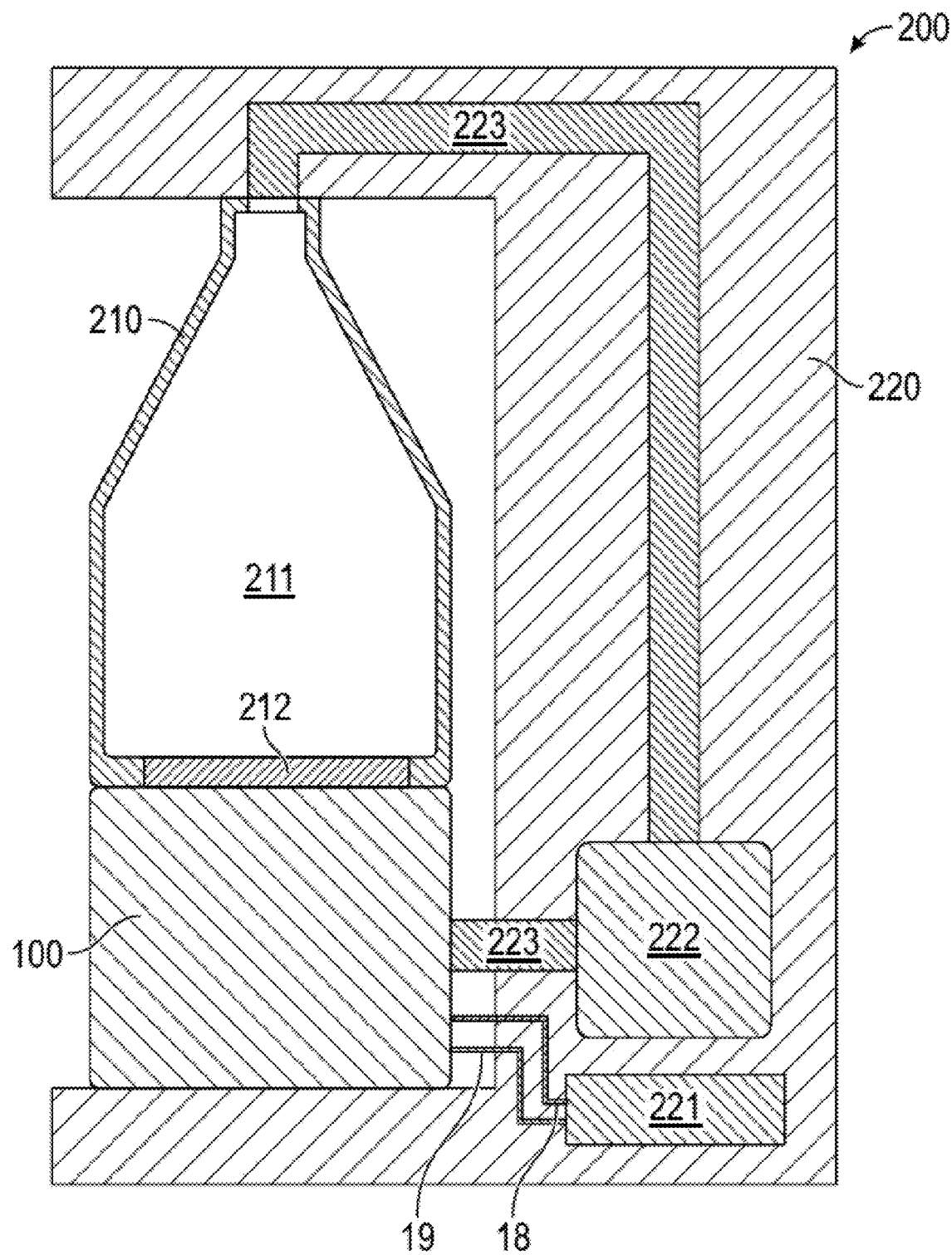
FIG. 4 depicts a schematic diagram of an example of a chlorine dioxide generating system according to various embodiments described herein.

FIG. 4 depicts an example of a chlorine dioxide generating system ("the system") 200 according to various embodiments. Generally, the system 200 may utilize one or more devices 100 to generate chlorine dioxide gas and to deposit the chlorine dioxide gas in a dispensing container 210 to facilitate the use of the chlorine dioxide gas for cleaning, disinfecting, sanitizing, oxidant of water, sterilization, oxidizing and other purposes.

In some embodiments, the system 200 may comprise a device 100 which may be configured to generate chlorine dioxide gas via electrolysis. A dispensing container 210 may be in communication with the device 100 so that the chlorine dioxide gas may enter a dispensing cavity 211 of the dispensing container 210. The dispensing cavity 211 may include a liquid, such as water, which the chlorine dioxide gas may be infused into. The system 200 may include an activator 220 which may supply electricity to the anode lead 18 and cathode lead 19 of the device 100 to enable electrolysis. In preferred embodiments, the system 200 may comprise a dispensing container 210 having a body and a dispensing hydrophobic membrane 212 which may be coupled to the body and placed on a device 100 so that the chlorine dioxide gas may pass through a hydrophobic membrane 17 of the device 100 and into the dispensing cavity 211 via the dispensing hydrophobic membrane 212. In other words, the hydrophobic membrane 212 may be configured to receive the chlorine dioxide gas from the device 100 therethrough. In other embodiments, a device 100 may be placed within the dispensing cavity 211 and into a liquid, such as water, which the chlorine dioxide gas may be infused into. The system 200 may include an activator 220 which may supply electricity to the anode lead 18 and cathode lead 19 of the device 100 to enable electrolysis so that the chlorine dioxide gas produced in the dispensing cavity 211 may be infused into the liquid within the dispensing cavity 211.

A system 200 may comprise one or more dispensing containers 210 which may be configured to contain a liquid, and be used to contain chlorine dioxide gas produced by a device 100. Each dispensing container 210 may include a dispensing cavity 211 that may be configured to hold or contain a desired volume of a liquid, such as water, into which chlorine dioxide gas may be dissolved or infused. A dispensing container 210 may be configured in any shape and size so as to have a dispensing cavity 211 of any shape and size. In preferred embodiments, a dispensing container 210 may be configured generally as a spray bottle preferably having threading or other removable coupling method disposed along its upper portions. This may allow the dispensing container 210 to be removably coupled to a spray nozzle, lid, portions of an activator 220, or other objects. It should be understood that a dispensing container 210 may be configured as any type of container preferably suitable for being held or manipulated by an individual.

A dispensing container 210 may be made from or may comprise substantially rigid materials, such as metal and metal alloys, hard plastics, including polyethylene (PE), Ultra-high-molecular-weight polyethylene (UHMWPE, UHMW), polypropylene (PP) and polyvinyl chloride (PVC), polycarbonate, nylon, hard rubbers; cushioning materials, such as silicone foams, rubber foams, urethane foams including plastic foams, neoprene foam, latex foam rubber, polyurethane foam rubber, or elastomer materials such as elastic plastics, elastic silicone, elastic rubbers; and/or any other material including combinations of materials.

In preferred embodiments, a dispensing container 210 may comprise a dispensing hydrophobic membrane 212 that may be disposed on lower portions of the dispensing container 210 and which may be in communication with the dispensing cavity 211. The hydrophobic membrane 212 may be configured to receive the chlorine dioxide gas therethrough in order to produce a cleaning solution with the liquid therein. This may allow the dispensing container 210 to be placed on or supported on a device 100 so that the hydrophobic membrane 17 of the device 100 and the dispensing hydrophobic membrane 212 of the dispensing container 210 are aligned to allow chlorine dioxide gas to pass from the device 100 into the dispensing cavity 211 via the hydrophobic membranes 17, 212. By positioning a hydrophobic membrane 212 on lower portions of a dispensing container 210, a liquid in the dispensing cavity 211 may rest on the hydrophobic membrane 212 so that as chlorine dioxide gas passes into the dispensing cavity 211 it may flow through the liquid to dissolve into the liquid. A dispensing hydrophobic membrane 212 may comprise any suitable hydrophobic membrane, such as which may be used to from a hydrophobic membrane 17 of a device 100.

An activator 220 may comprise a power source 221 which may be configured to supply electricity to the device 100, such as via an anode lead 18 and cathode lead 19, so that the device 100 may perform electrolysis on the reagents 15, 16, within the device 100 to produce chlorine dioxide gas. In some embodiments, a power source 221 may comprise a battery, such as a lithium ion battery, nickel cadmium battery, alkaline battery, or any other suitable type of battery, a fuel cell, a capacitor, a super capacitor, or any other type of energy storing and/or electricity releasing device. In further embodiments, a power source 221 may comprise a power cord, transformer, kinetic or piezo electric battery charging device, a solar cell or photovoltaic cell, and/or inductive charging or wireless power receiver. In further embodiments, a power source 221 may comprise a power charging and distribution module which may be configured to control the recharging of the power source 221, discharging of the power source 221, and/or distribution of power to one or more components of the device 100 and system 200 that may require electrical power.

Figure 5:
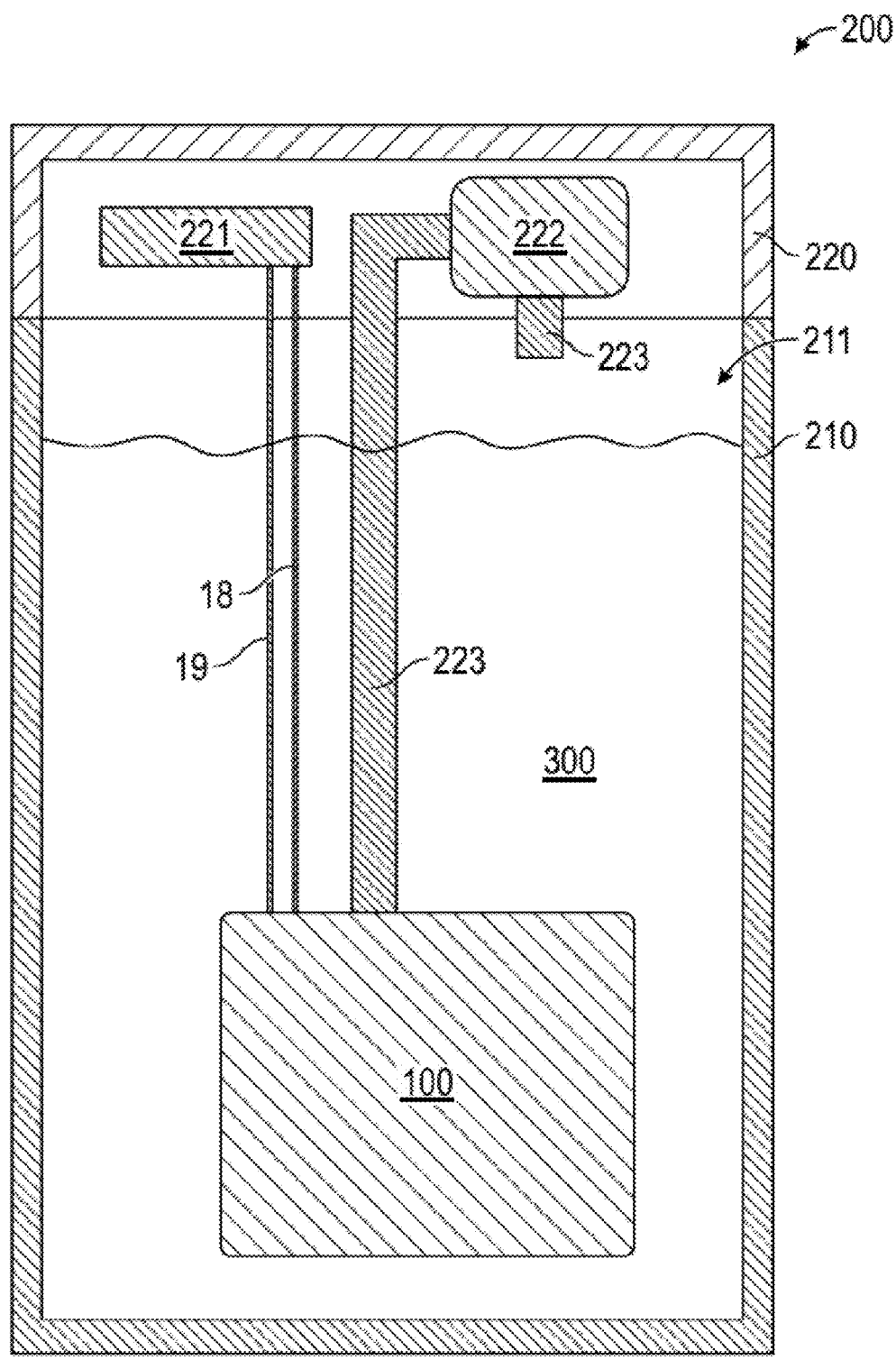
FIG. 5 depicts a schematic diagram of another example of a chlorine dioxide generating system according to various embodiments described herein.

An activator 220 may be configured in any size and shape. In preferred embodiments and as shown in FIG. 4, an activator 220 may comprise a relatively larger size so as to provide a platform upon which a device 100 may be placed or supported while also allowing a dispensing container 210 to be placed or supported on the device 100. The dispensing container 210 may be in fluid communication with the chlorine dioxide gas generating device 100, and may be configured to receive the chlorine dioxide gas after the chlorine dioxide gas has exited the device 100. A larger sized activator 220 may also allow one or more optional components of the system 200 to be placed within the activator 220. In further embodiments and as shown in FIG. 5, an activator 220 may comprise a relatively smaller size so as to allow the activator 220 to be coupled to a dispensing container 210 as a lid while the device 100 may be placed inside a dispensing cavity 211 of the dispensing container 210. In this manner, the device 100 may infuse a liquid 300, such as water, within the dispensing cavity 211 with chlorine dioxide gas. For example, this may allow the system 200 to be used to optionally make sanitizer or disinfectant to apply to surfaces and optionally to generate chlorine dioxide gas in a water liquid 300 from questionable water sources to render the water liquid 300 drinkable. In the embodiment of FIG. 5, the dispensing container 210 is configured to contain a liquid, and the chlorine dioxide gas generating device 100 is located inside the dispensing container 210 such that the chlorine dioxide gas generating device 100 is submerged by the liquid.

Preferably, an activator 220 may be made from or may comprise substantially rigid materials, such as metal and metal alloys, hard plastics, including polyethylene (PE), Ultra-high-molecular-weight polyethylene (UHMWPE, UHMW), polypropylene (PP) and polyvinyl chloride (PVC), polycarbonate, nylon, hard rubbers, wood, other plant based materials; cushioning materials, such as silicone foams, rubber foams, urethane foams including plastic foams, neoprene foam, latex foam rubber, polyurethane foam rubber, or elastomer materials such as elastic plastics, elastic silicone, elastic rubbers; and/or any other material including combinations of materials.

In some embodiments, an activator 220 may comprise a vacuum pump 222 which may be in communication with a device 100 and a dispensing container 210. The vacuum pump 222 may be configured to draw a portion of the chlorine dioxide gas received in the dispensing container first into the chlorine dioxide gas generating device 100, and then back into the dispensing container 210 in order to concentrate the chlorine dioxide gas in the liquid in the dispensing container 210. A vacuum pump 222 may be configured to create a vacuum in the dispensing cavity 211 of a dispensing container 210 which may draw chlorine dioxide gas that has not been dissolved in a liquid in the dispensing cavity 211 out of the dispensing cavity 211. This chlorine dioxide gas may then be recirculated into the dispensing cavity 211, preferably by being recirculated into the device 100 and then into the dispensing cavity 211 via the hydrophobic membranes 17, 212. In this manner, the vacuum pump 222 may be used to concentrate chlorine dioxide gas within the liquid in the dispensing cavity 211.

In some embodiments, an activator 220 may comprise one or more gas conducting conduits 223 which may be used to communicate chlorine dioxide gas, air, and other materials from a dispensing container 210 to be recirculated through a device 100 and/or the dispensing container 210 as motivated by a vacuum pump 222. Gas conducting conduits 223 may be in fluid communication with the dispensing container 210 and the vacuum pump 222 in order to allow the vacuum pump to pull the chlorine dioxide gas from the dispensing container 210 into the chlorine dioxide gas generating device 100. Conducting conduits 223 may comprise any type of pipe or conduit suitable for contacting chlorine dioxide gas, such as Polyurethane tubing and fittings, Poly Vinyl Chloride (PVC) pipe and fittings, Chlorinated Poly Vinyl Chloride (CPVC) pipe and fittings, cross-linked polyethylene (PEX) pipe and fittings, polyethylene pipe and fittings, vinyl pipe and fittings, or any other suitable type of pipe or conduit.

A vacuum pump 222 may comprise any device which may be suitable for motivating chlorine dioxide gas. In preferred embodiments, a vacuum pump 222 may comprise a miniature vacuum pump, such as a 100 KPa 5V-6V DC Miniature Vacuum Pump with a 370 motor. In further embodiments, a vacuum pump 222 may comprise a magnetic drive pump, positive displacement pump such as a rotary vane pump, a liquid ring pump, a piston pump, a scroll pump, a screw pump, a Wankel pump, an external vane pump, a roots blower or booster pump, a multistage roots pump, a Toepler pump, a lobe pump, or any other suitable positive displacement pump. In alternative embodiments, a vacuum pump 222 may comprise a momentum transfer pump, a regenerative pump, a venturi vacuum pump, an entrapment pump, or any other type of pump which may be suitable for motivating chlorine dioxide gas through a device 100 and/or dispensing container 210. Optionally, a vacuum pump 222 may comprise a motor driven vacuum generating device such as a blower fan, a vane pump, a diaphragm pump, a liquid ring pump, a piston pump, a scroll pump, a screw pump, a Wankel pump, a roots blower or booster pump, a multistage roots pump, a Toepler pump, a lobe pump, or other suitable pump may be used.

Example Implementation

In detail, chlorine dioxide gas was made from 10 grams ACS Reagent grade sodium chlorite (second reagent 16) and 50 mm Type I Ultra-Pure Water (first reagent 15) as defined by the American Society for Testing and Materials (ASTM) as having a resistivity of >18 MΩ-cm, a conductivity of <0.056 µS/cm and <50 ppb of Total Organic Carbons (TOC). A measured amount was created and filled into a small electro-bath cartridge. The electrolysis was operated by 5 V and 1 A current. During electrolysis, the chlorine dioxide gas was released from the device 100 using a hydrophobic membrane 17 at a rate of 0.05 ppm. This provides for the ability to control the ppm of ultrapure chlorine dioxide gas generation to be controlled and specific by a ratio of Type I Ultra-Pure Water to ACS Reagent Grade sodium chlorite and voltage and amp regulation above 1.5 V and under 1 A multiplied by time for specific ppm use. It will also be appreciated that other suitable voltage and amperage combinations are contemplated herein to perform the desired electrolysis function based on the output needs, associated materials, and reagents used.

Release of chlorine dioxide gas was into a chamber of Ultra-Pure Water to make a solution chlorine dioxide gas for selected uses. The chemical composition of the chlorine dioxide gas solution was determined according to a standard method based on the final product output and use. The resulting solution contained 0.05 ppm $ClO_2$. The total impurities concentration is significantly lower than in the case of other $ClO_2$ generators because the first reagent 15 did not contain any sodium chloride (NaCl) or other contaminants in the water. The chlorine dioxide solution was produced by using only measured % $NaClO_2$ in solution with Type I water Ultra-Pure Water, with no other additive, which is an obvious advantage.

Electrolysis of Ultra-Pure Water has a conductivity of 18.24 MΩ cm requires excess energy in the form of over-potential to overcome various activation barriers. Without the excess energy the electrolysis of ultra-pure water occurs very slowly or not at all. This is in part due to the limited self-ionization of water. Ultra-Pure water has an electrical conductivity about one millionth that of seawater.

By adding the ACS reagent grade sodium chlorite as the second reagent 16 into a first reagent 15 of Type I Ultra-Pure Water to form a solution, electrolysis can occur, even at a low current level. This electrolysis is acting as the catalyst in the solution of Type I Ultra-Pure Water and ACS Reagent grade sodium chlorite, and the generation of chlorine dioxide gas is from the anode 18 side of the electrolytic method. Since little or no electrolytic activity occurs on the cathode 19 side, very little impurities are generated. By separating the cathode 19 and anode 18 with a Proton Exchange Membrane (PEM) 20, the reassurance of separating the chlorine dioxide gas from impurities is established. Based on end users' needs and purity level, the PEM 20 may or may not be required.

While some exemplary shapes and sizes have been provided for elements of the device 100, it should be understood to one of ordinary skill in the art that a housing 11, cavity 12, anode 13, cathode 14, hydrophobic membrane 17, proton exchange membrane 20, and any other element described herein may be configured in a plurality of sizes and shapes including "T" shaped, "X" shaped, square shaped, rectangular shaped, cylinder shaped, cuboid shaped, hexagonal prism shaped, triangular prism shaped, or any other geometric or non-geometric shape, including combinations of shapes. It is not intended herein to mention all the possible alternatives, equivalent forms or ramifications of the invention. It is understood that the terms and proposed shapes used herein are merely descriptive, rather than limiting, and that various changes, such as to size and shape, may be made without departing from the spirit or scope of the invention.

Additionally, while some materials have been provided, in other embodiments, the elements that comprise the device 100 may be made from or may comprise durable materials such as aluminum, steel, other metals and metal alloys, wood, hard rubbers, hard plastics, fiber reinforced plastics, carbon fiber, fiber glass, resins, polymers or any other suitable materials including combinations of materials. Additionally, one or more elements may be made from or may comprise durable and slightly flexible materials such as soft plastics, silicone, soft rubbers, or any other suitable materials including combinations of materials. In some embodiments, one or more of the elements that comprise the device 100 may be coupled or connected together with heat bonding, chemical bonding, adhesives, clasp type fasteners, clip type fasteners, rivet type fasteners, threaded type fasteners, other types of fasteners, or any other suitable joining method. In other embodiments, one or more of the elements that comprise the device 100 may be coupled or removably connected by being press fit or snap fit together, by one or more fasteners such as hook and loop type or Velcro® fasteners, magnetic type fasteners, threaded type fasteners, sealable tongue and groove fasteners, snap fasteners, clip type fasteners, clasp type fasteners, ratchet type fasteners, a push-to-lock type connection method, a turn-to-lock type connection method, a slide-to-lock type connection method or any other suitable temporary connection method as one reasonably skilled in the art could envision to serve the same function. In further embodiments, one or more of the elements that comprise the device 100 may be coupled by being one of connected to and integrally formed with another element of the device 100.

In another example, a method of producing a cleaning solution with the system 200 includes the steps of passing an electric current from the power source 221 into the anode 13 and the cathode 14, and in response, generating chlorine dioxide gas via electrolysis with the first and second reagents 15, 16; delivering the chlorine dioxide gas from the chlorine dioxide gas generating device 100 into the dispensing container 210; and infusing substantially all of the chlorine dioxide gas into the liquid in the dispensing container 210 in order to produce the cleaning solution. The method may further include passing the chlorine dioxide gas through a hydrophobic membrane 17 of the chlorine dioxide gas generating device 100, passing the chlorine dioxide gas through a hydrophobic membrane 212 of the dispensing container 210. The method may also include drawing a portion of the chlorine dioxide gas in the dispensing container 210 back into the chlorine dioxide gas generating device 100 with the vacuum pump 222, and drawing the portion of the chlorine dioxide gas from the chlorine dioxide gas generating device 100 back into the dispensing container 210 in order to concentrate the cleaning solution. Moreover, as shown in FIG. 5, the method may also include submerging the chlorine dioxide gas generating device 100 in the liquid of the dispensing container 210.

In one example, the first and second reagents 15, 16 are configured to generate the chlorine dioxide gas out of the solution containing the first and second reagents 15, 16 without additional reagents being circulated into the housing. In other words, the device 100 is configured as a stand-alone pod that is separately able to generate chlorine dioxide gas until the encapsulated reagents 15, 16 therein expire. Additionally, the chlorine dioxide gas is configured to exit the housing 11 through the hydrophobic membrane 17 such that the chlorine dioxide gas is generated in a controllable, start and stop manner. In this manner the chlorine dioxide gas generating device 100 (e.g., and devices 400, 500, each of which may be substituted into the chlorine dioxide gas generating system 200 for the chlorine dioxide gas generating device 100, discussed below) is advantageously configured to provide a disposable and, in one example, non-refillable device for chlorine dioxide gas to be generated, e.g., and also generated in a portable manner.

Moreover, the housing 11 may, before chlorine dioxide gas is generated, contain a first amount of the first reagent 15 and a second amount of the second reagent 16. As the electric current is being passed into the anode 13 and the cathode 14, the first and second amounts of the first and second reagents 15, 16 each continually decrease until the first and second amounts are about zero, as long as a voltage is applied to the anode 13 and the cathode 14. It will also be appreciated that the hydrophobic membrane 17 may include first and second surfaces (shown but not labeled) facing away from one another, with the first surface facing the cavity 12 of the housing 11.

Continuing to refer to the chlorine dioxide gas generating device 100, it will be appreciated that the electric current configured to be passed into the anode 13 and the cathode 14 is a catalyst, and in one example is the only catalyst (e.g., the disclosed reaction, in one example, does not require separate acidic agents to generate the chlorine dioxide gas) for the generation of the chlorine dioxide gas. Put another way, the chlorine dioxide gas generating device 100 may be configured to generate a predetermined quantity of the chlorine dioxide gas out of the reagent solution, and after the predetermined quantity of the chlorine dioxide gas has been generated, an additional electric current passed into the anode 13 and the cathode 14 does not generate additional chlorine dioxide gas.

Figure 6:
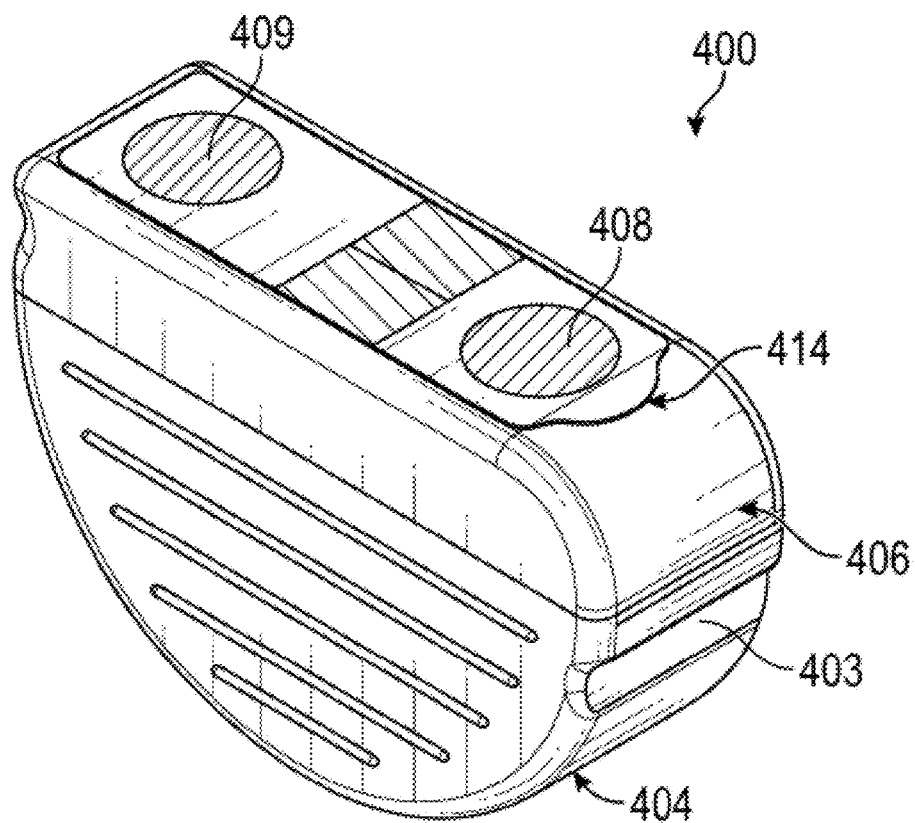
FIGS. 6 and 7 depict isometric and exploded isometric views, respectively, of another chlorine dioxide gas generating device, in accordance with another non-limiting embodiment of the disclosed concept.
Figure 7:
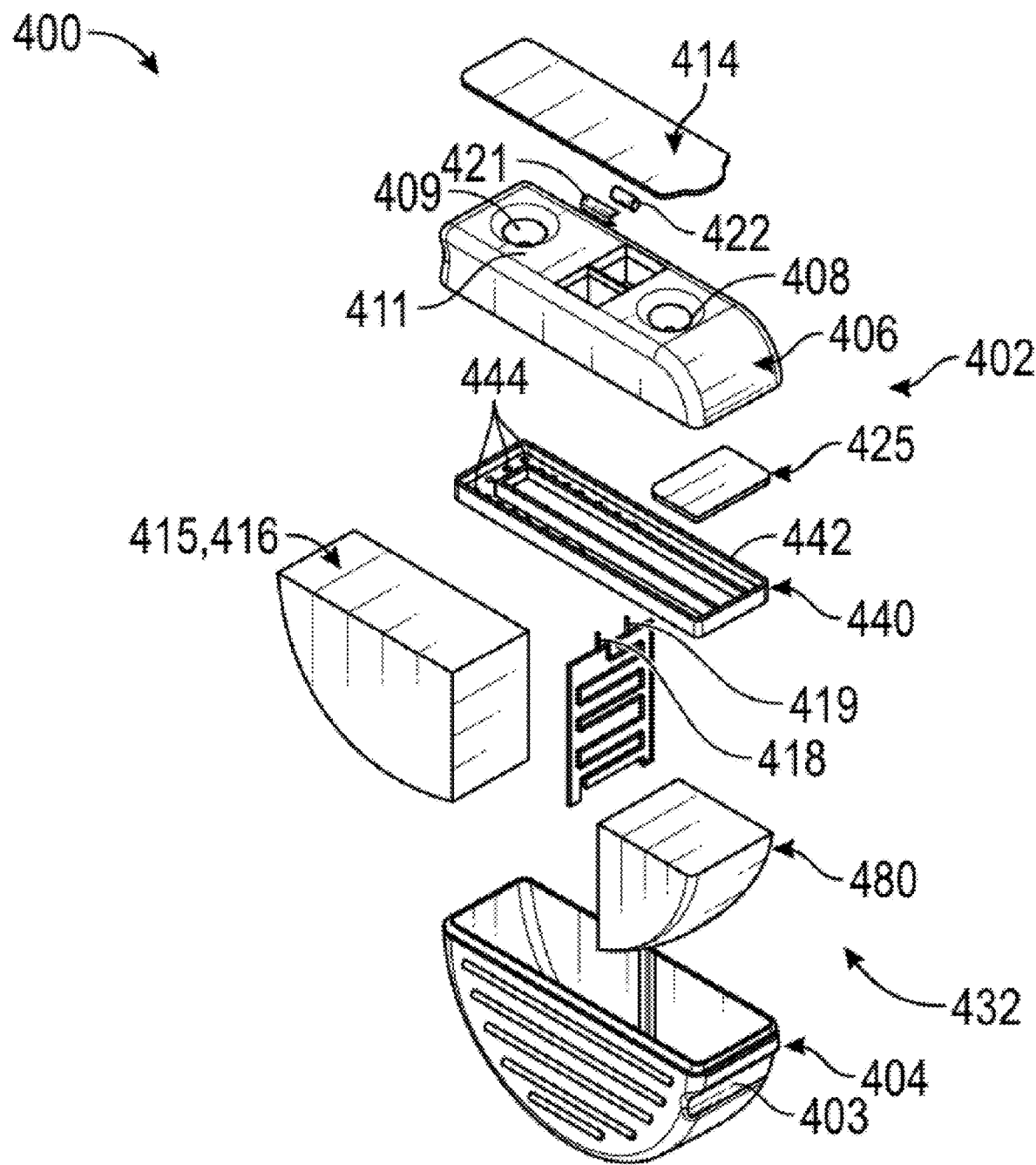

FIGS. 6 and 7 show different views of another chlorine dioxide gas generating device 400, structured similar to the chlorine dioxide gas generating device 100, discussed above, in accordance with another non-limiting embodiment of the disclosed concept. The device 400 is configured to generate chlorine dioxide gas via electrolysis with respect to first and second reagents 415, 416 (e.g., sodium chlorite and water), responsive to a current being passed into an anode 418 and a cathode 419. As shown most clearly in FIG. 7, the chlorine dioxide gas generating device 400 includes a housing 402 which, in one example, includes a body 404, a lid 406 coupled to the body 404 such that the lid 406 and the body 404 form a cavity. The lid 406 may have a number of through holes 408, 409 for allowing chlorine dioxide gas to exit the housing 402 and for allowing additional gas to enter the housing, respectively (e.g., chlorine dioxide gas may exit through the first hole 408 before being delivered to, for example, a dispensing container 210 which may be a spray bottle, and additional gas may be pulled into the housing through the second through hole 409 via a vacuum pump (e.g., vacuum pump 222).

Figure 8:
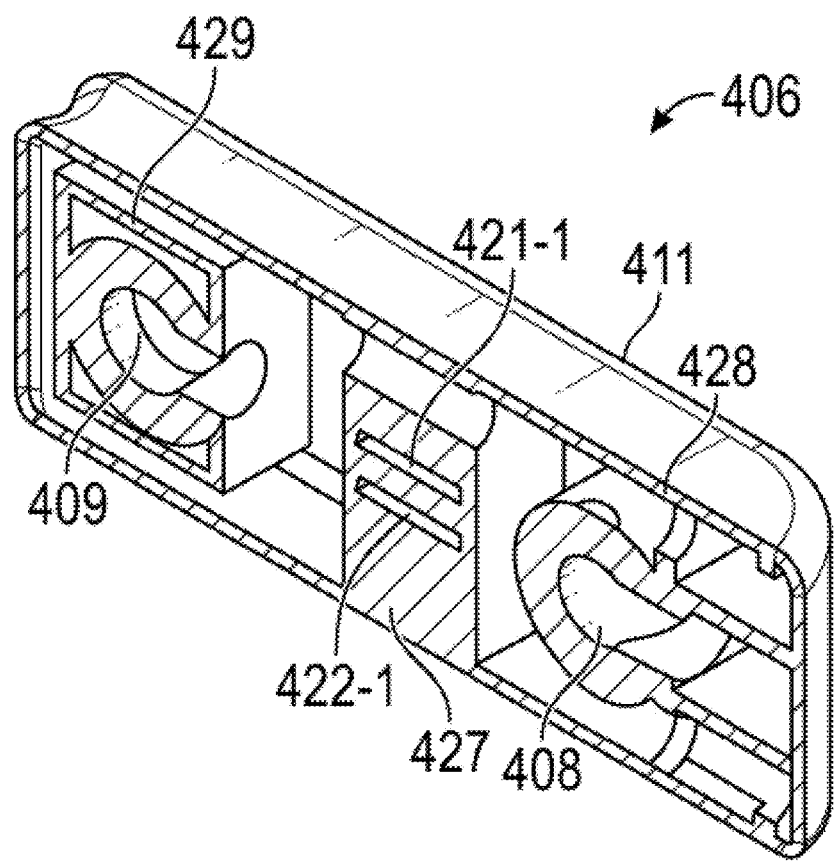
FIG. 8 depicts a rear isometric view of a lid for the housing of the chlorine dioxide gas generating device of FIGS. 6 and 7.
Figure 9:
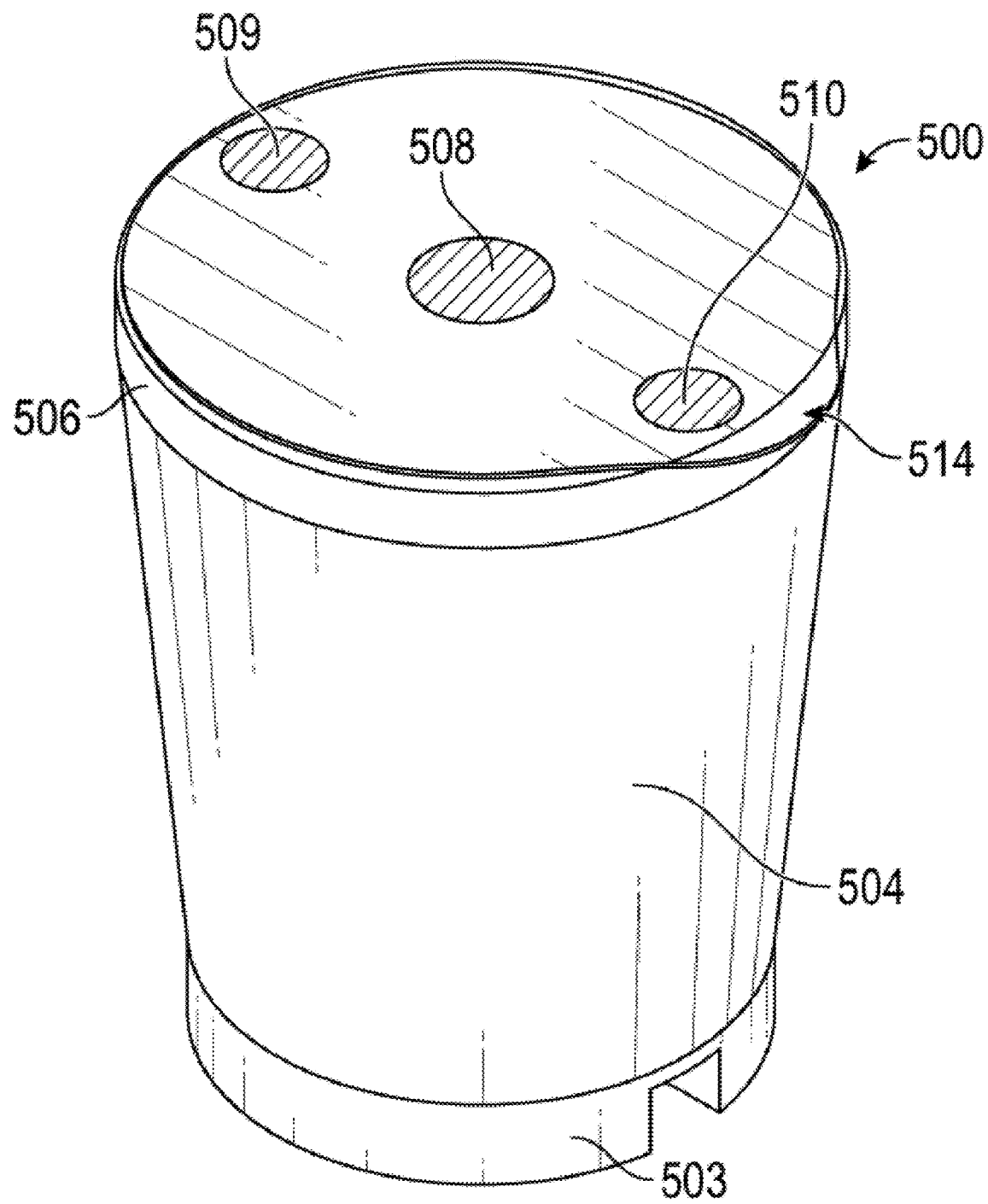
FIGS. 9-12 depict assembled isometric, two exploded isometric, and section views, respectively, of another chlorine dioxide gas generating device, with certain elements missing in certain Figures for ease of illustration, in accordance with another non-limiting embodiment of the disclosed concept.

In one example embodiment, the housing further includes at least one sealing member 414 sealed to the lid 406 over the first through hole 408 and the second through hole 409. The at least one sealing member 414 prevents evaporation of first and second reagents (denoted with numerals 415, 416 in FIG. 7 to represent one homogenous solution), thereby prolonging shelf life of the device 400. The reagents 415, 416 may be located in the cavity and be sodium chlorite and water, respectively, in one example (e.g., reagents which are configured to generate chlorine dioxide gas, responsive to an electric current being passed through an anode and cathode 418, 419). When a user desires to generate chlorine dioxide gas with the device 400, the user can peal off the sealing member 414 (e.g., the sealing member 414 may be adhesively coupled or otherwise bonded to a top side 411 of the lid 406 in a sealed manner) and/or puncture the sealing member 414 proximate the through holes 408, 409, thereby allowing gas to enter the second through hole 409 (e.g., from a vacuum pump 222) and chlorine dioxide gas to exit the housing 402 through the first through hole 408. It will also be appreciated that a suitable alternative chlorine dioxide gas generating device may include multiple sealing members, one for each of the through holes 408, 409, without departing from the scope of the disclosed concept. Additionally, the device 400 may also have anode and cathode leads 421, 422, which function similar to the anode and cathode leads 18, 19 of the device 100, discussed above. These leads 421, 422 and/or the anode and cathode 418, 419 may extend through additional through holes 421-1, 422-1 of the lid 406, as shown in FIG. 8.

It will also be appreciated that the hydrophobic membrane 425 of the device 400 is configured to be sealed, in one example, to a rear side 427 of the lid 406 at the first through hole 408. See FIG. 8, for example, which shows the rear side 427 of the lid 406. In this manner, the generated chlorine dioxide gas may be configured to exit the housing 402 by first passing through the hydrophobic membrane 425, and then second passing through the first through before being delivered to, for example, a dispensing container or other suitable application.

In accordance with the disclosed concept, the device 400 advantageously further includes a fluid control apparatus 432 located within the cavity of the housing 402 and configured to increase a rate of release of the chlorine dioxide gas out of the solution containing the first and second reagents 415, 416, and reduce an amount of liquid pulled into a wall of the hydrophobic membrane 425. In one example, the fluid control apparatus 432 includes a bubbler device 440 and a guard member (e.g., without limitation, mesh member 480) each located within the cavity of the housing 402 (e.g., press fit into the housing 402 or otherwise bonded (e.g., ultrasonically welded and/or via adhesives) to the housing 402). It will thus be appreciated that the bubbler device 440 includes a body 442 having a plurality of through holes 444 that are configured to increase the rate of release of the chlorine dioxide gas. Furthermore, the mesh member 480, which may be either coupled to the housing 402 or maintained in the housing 402 via a press fit mechanism, is configured to diffuse splashing of the solution (e.g., the solution containing the first and second reagents 415, 416), responsive to the increase in the rate of release of the chlorine dioxide gas by the bubbler device 440, thereby reducing the amount of liquid pulled into the wall of the hydrophobic membrane 425. In one example, the anode 418 and the cathode 419 are configured to extend through a central through hole of the bubbler device 440, and may also be coupled to the body 404 of the housing 402 via a tongue and groove mechanism (shown but not labeled).

The bubbler device 440 advantageously functions to excite the chlorine dioxide gas being generated in the cavity of the housing 402 via electrolysis. More specifically, as additional gas is pulled through the second through hole 409 via, for example, the pump 222, that additional gas is received by the plurality of through holes 444 therethrough. In this manner, the additional gas is configured to gain velocity, e.g., via Bernoulli's principle, and be passed into the liquid solution that is comprised of the first and second reagents 415, 416 in a turbulent manner that, in one example, causes the chlorine dioxide gas to be released significantly faster (e.g., at least 10 times faster in one example).

Once the chlorine dioxide gas is generated via electrolysis, and excited by the additional gases passing through the through holes 444, microbubbles containing the chlorine dioxide gas are popped (e.g., via the fast-moving gases passing through the holes 444). Subsequently, any remaining portion of the solution containing the reagents 415, 416 which may otherwise splash the hydrophobic membrane 425 is prevented from doing so via the mesh member 480 (e.g., the mesh member 480 diffuses any splashing). In this manner, the mesh member 480, which may be a porous and/or fibrous material and/or a sponge, is configured to diffuse splashing of a solution containing the first and second reagents 415, 416. As a result, a gas-gas fluid of chlorine dioxide gas is easily configured to pass through the mesh member 480, before exiting the housing 402 through the hydrophobic membrane 425 and then the first through hole 408. At the same time as the gas-gas fluid of chlorine dioxide gas is passing through the mesh member 480 and out of the housing 402, liquid fluids are caused to be prevented from engaging the hydrophobic membrane 425 via the mesh member 480. In turn, the life and integrity of the hydrophobic membrane 425 is configured to be significantly improved by having liquid fluids not being infused into its wall.

It will also be appreciated that the bubbler device 440 may be strategically positioned in the housing 402. More specifically, the rear side 427 of the lid 406 may be located in the cavity of the housing 402, and the top side 411 may define a portion of an exterior of the housing 402. The rear side 427 of the lid 406 may include first and second adjacent regions 428, 429. The hydrophobic membrane 425 may be coupled to the first region 428, and each of the plurality of through holes 444 of the bubbler device 440 may overlay the second region 429 of the rear side 427 of the lid 406. Thus, additional gas entering the housing through the second through hole 409 may readily be directed directly into the through holes 444. Furthermore, as will be appreciated with reference to FIG. 7, lid 406, the body 404 of the housing 402, and the bubbler device 440 each have a perimeter portion substantially overlaying and being shaped the same (e.g., rectangular-shaped) as one another in order to allow the bubbler device 440 to be substantially maintained across the cavity of the housing 402.

Referring again to FIG. 6, as shown, the body 404 of the housing 402 has a groove 403 on an exterior surface thereof in order to mate with a corresponding lip of a housing of a chlorine dioxide gas generating system via a snap-fit mechanism, thereby allowing the first and second through holes 408, 409 to be pressure sealed therebetween. In one example (not shown), the exterior surface of the body has a detent and the housing of the system has a groove, and in another example (not shown) an exterior surface of the lid 406 has a groove or detent configured to mate with a corresponding groove or detent of a housing of a system, without departing from the scope of the disclosed concept.

Figure 10:
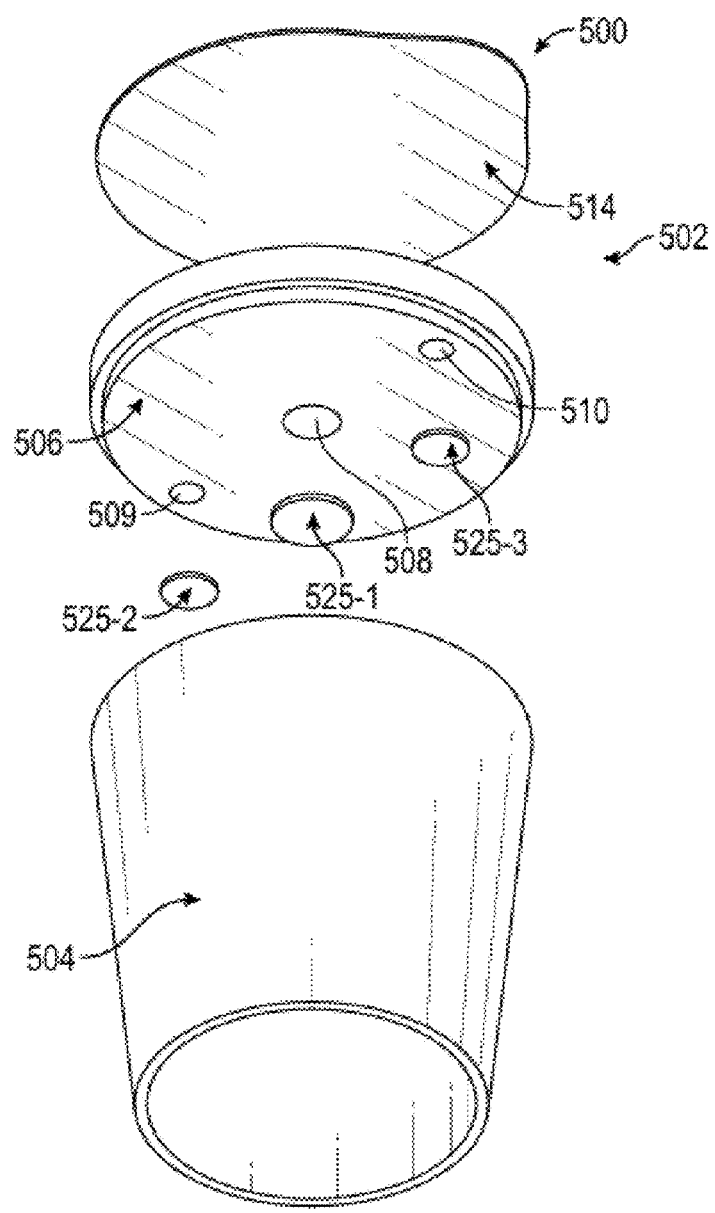
Figure 11:
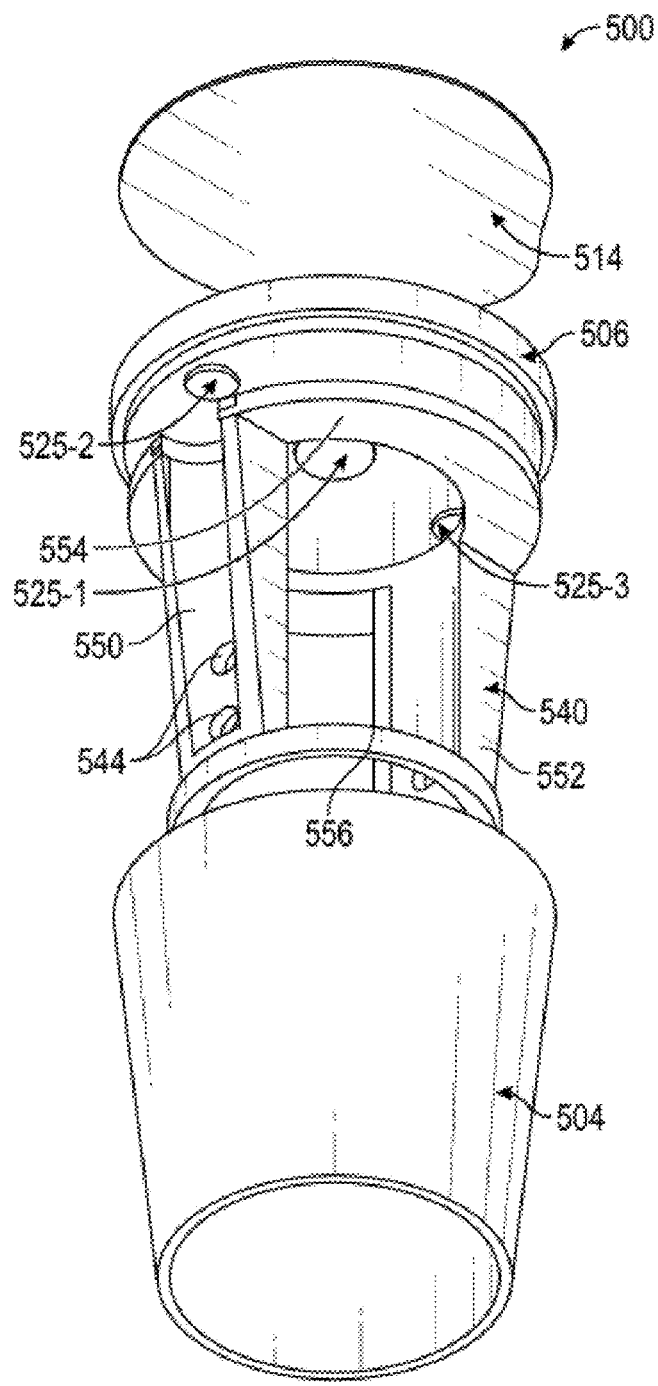
Figure 12:
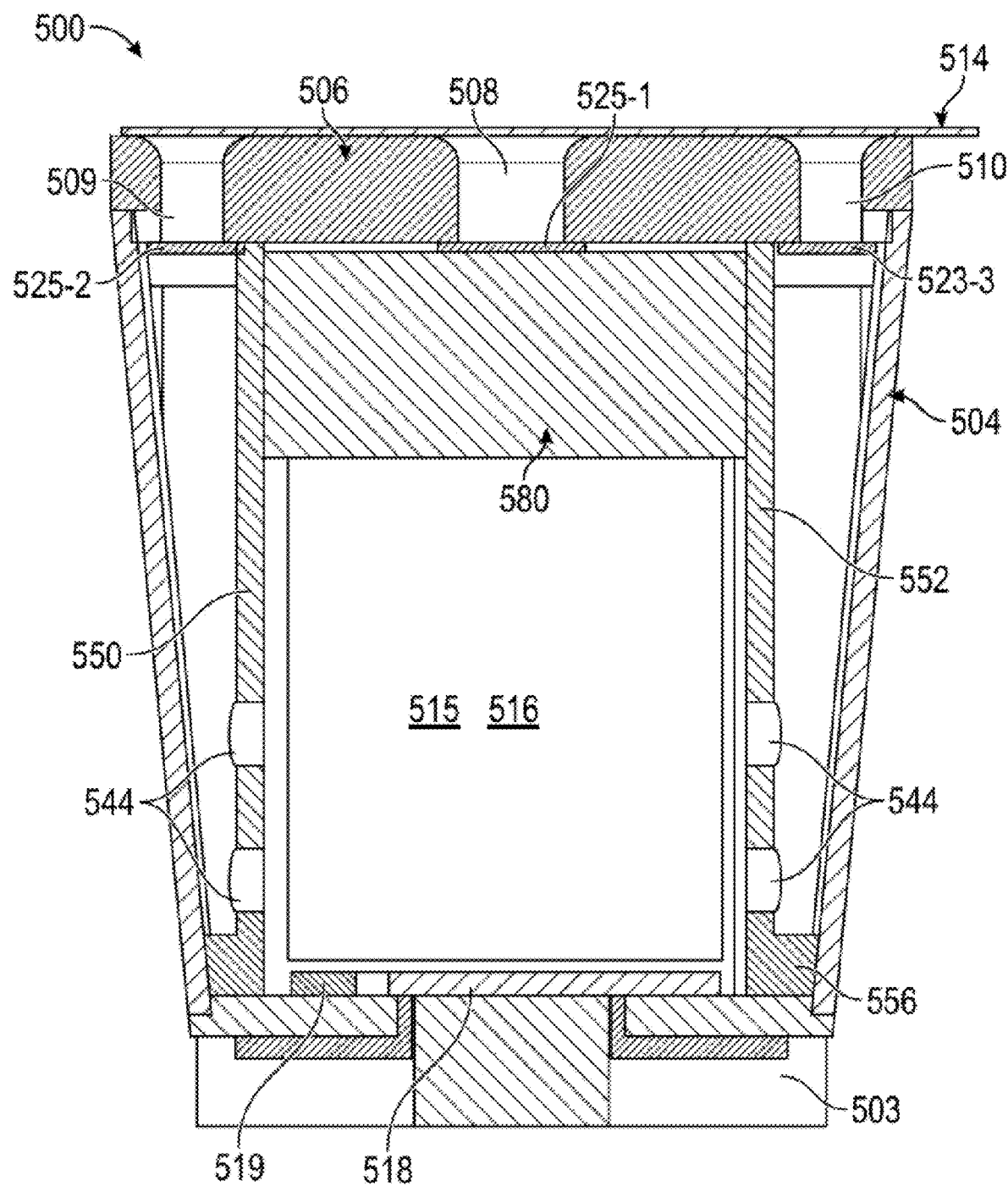

FIGS. 9-12 show various views of another chlorine dioxide gas generating device 500, in accordance with another non-limiting embodiment of the disclosed concept. The device 500 functions similar to the device 400 (e.g., fluid control apparatus in form of bubbler device and guard member), and like numbers represent like features. The device 500 includes a housing 502 having a base 503, a body 504 having a through hole at a bottom and coupled to the base 503 (e.g., without limitation, via a threaded connection, snap-fit connection), and a lid 506, and a sealing member 514. Unlike the device 400, the lid 506 of the device 500 has first, second, and third through holes 508, 509, 510, with the first, central through hole 508 configured to allow chlorine dioxide gas to exit the housing 502, and the second and third through holes 509, 510 configured to receive additional gas into the housing 502. As shown in FIG. 10, the device 500 has a plurality of hydrophobic membranes 525-1, 525-2, 525-3. The second and third hydrophobic membranes 525-2, 525-3 may be located between first and second channel members 550, 552 of the bubbler device 540 and the second and third through holes 509, 510, respectively. Furthermore, in one example the device 500 further includes an anode 518 and a cathode 519 each maintained on the base 503 of the housing 502 and located in a cavity of the housing 502 (e.g., via the bottom through hole of the body 504) and spaced from one another (e.g., notice the air gap therebetween in FIG. 12), as shown in FIG. 12.

Figure 13:
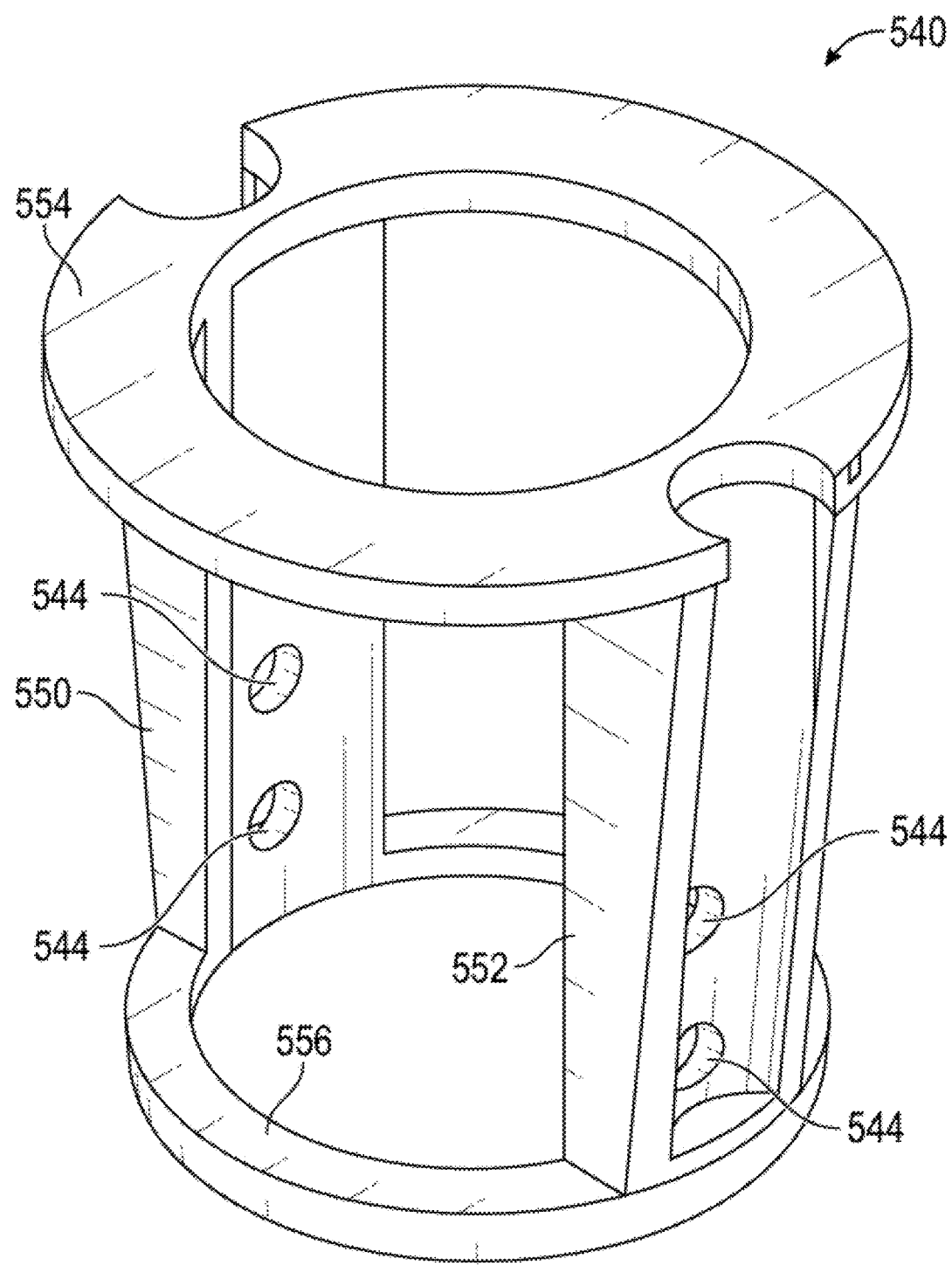
FIG. 13 depicts an isometric view of a bubbler device for the chlorine dioxide gas generating device of FIGS. 9-12.

Referring to FIG. 13, the bubbler device 540 has the first channel member 550, the second channel member 552, a top 554 extending from each of the first and second channel members 550, 552, and a support member 556 extending from each of the first and second channel members 550, 552 and located opposite the top 554. The support member 556 may be ring-shaped and configured to nest in the body 504 of the housing 502 in order to provide structural support thereto. The first and second channel members 550, 552 form first and second passages, respectively, each with the body 504 of the housing 502 (see, for example, FIG. 12, which shows two passages on the right and the left each which is defined by the body 504 of the housing 502 and a corresponding one of the channel members 550, 552. In one example, additional gas (e.g., from a vacuum pump 222) enters the housing 502 through the second and third through holes 509, 510 and enters the central passage by passing through the through holes 544 of the channel members 550, 552, thereby allowing the reagent solution to be excited and the rate of release of the associated chlorine dioxide gas to be increased.

Continuing to refer to FIG. 12, it will be appreciated that the first and second channel members 550, 552 and the body 504 of the housing together form the third passage, e.g., the passage which contains the solution comprising the first and second reagents 515, 516 (e.g., sodium chlorite and water). Thus, after the chlorine dioxide gas is generated in the third passage, and is excited by the rapid moving gas through the through holes 544, the chlorine dioxide gas is configured to exit the housing via the first through hole 508 after passing through the third passage. However, as the chlorine dioxide gas is exiting the third passage and being passed through the hydrophobic membrane 525-1, a guard member (e.g., mesh member 580) is configured to diffuse splashing of a solution containing the first and second reagents 515, 516, thereby reducing an amount of liquid engaging and/or entering a wall of the hydrophobic membrane 525-1, thus prolonging the life and integrity of the hydrophobic membrane 525-1. The mesh member may either be coupled to the third passage or maintained therein via a press fit mechanism. Additionally, the hydrophobic membrane 525-1 may be located between the mesh member and a portion of the lid 506 defining the first through hole 508.

It will also be appreciated that the sealing member 514 may be sealed to the lid 506 over the first, second and third through holes 508, 509, 510 in order to prevent evaporation of the first and second reagents.

Figure 14:
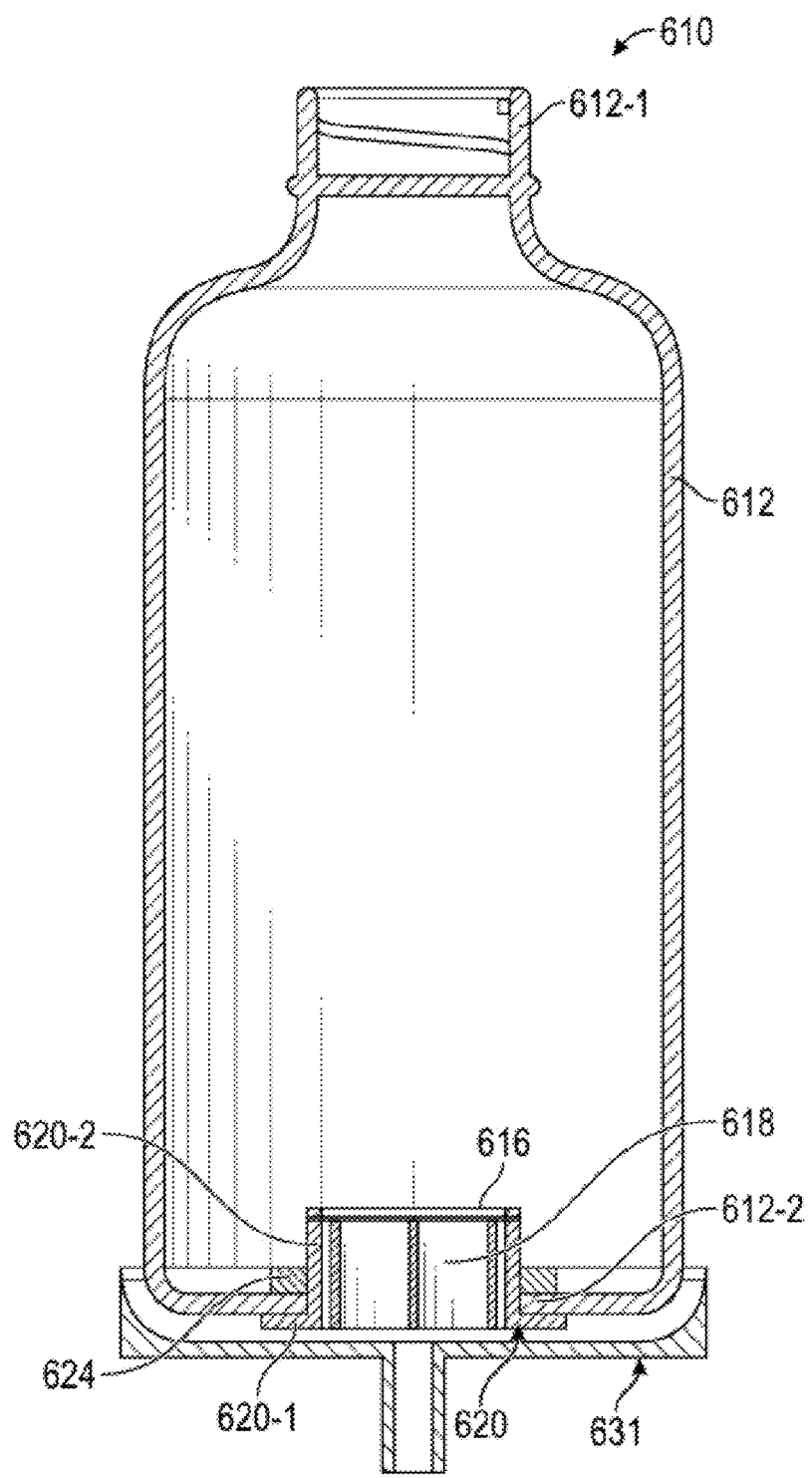
FIGS. 14 and 15 depict section and exploded isometric views, respectively, of a dispensing container, shown as employed with a mounting member, in accordance with one non-limiting embodiment of the disclosed concept.
Figure 15:
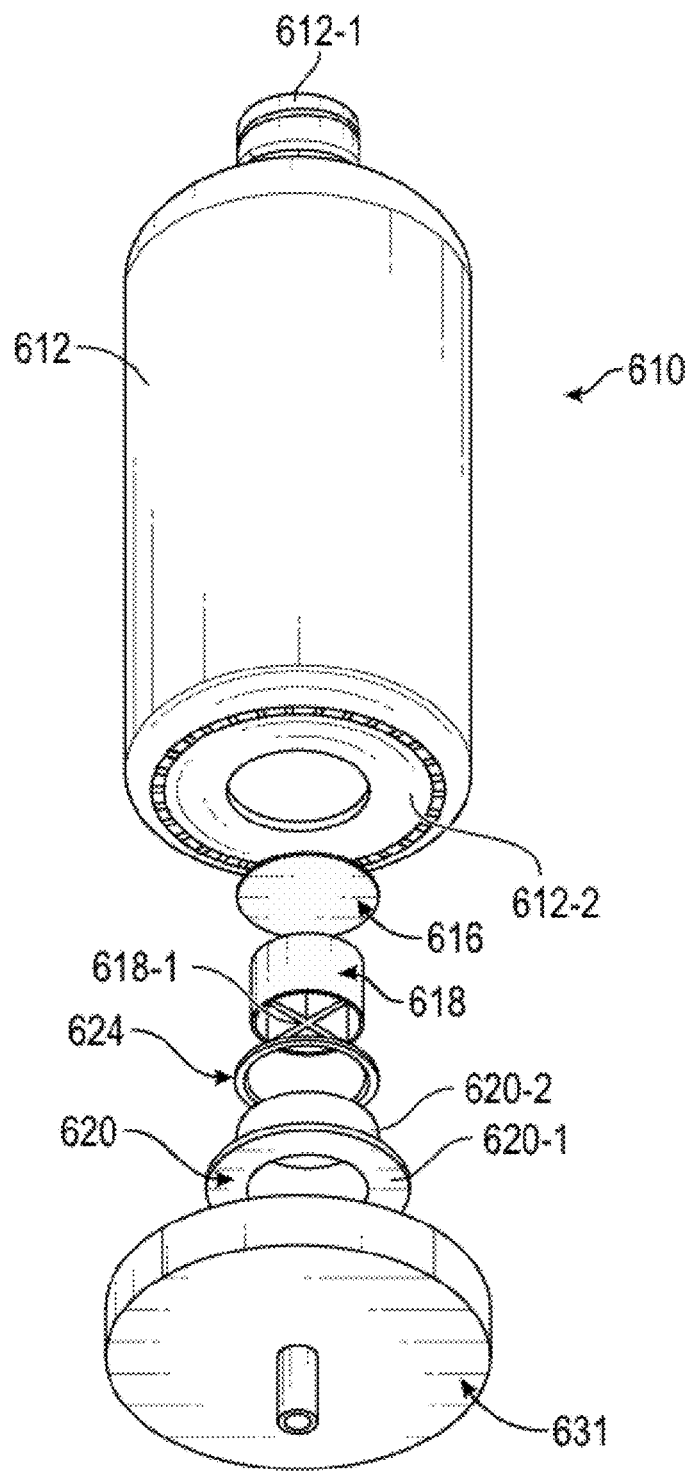

FIGS. 14 and 15 show section and exploded isometric views, respectively, of a dispensing container 610, shown as employed with a mounting member 631, and which functions similar to the dispensing container 210 (FIG. 4), e.g., is configured to receive generated chlorine dioxide gas therein in order to mix with a liquid (e.g., water), and be used for disinfectant purposes. In one example, the dispensing container 610 is a spray bottle including a bottle 612 having a first end 612-1 and an opposite, second end 612-2, wherein each has a through hole. The bottle 612 may be configured to contain a liquid (e.g., water) and be removably coupled to a spray nozzle at the first end 612-1.

Referring to FIG. 15, the dispensing container 610 further includes a hydrophobic membrane 616, a first interconnect component 620, a second interconnect component 618 configured to be threadably coupled to an interior of the first interconnect component 620, and a locking member 624. In one example, the first interconnect component 620 is coupled to the second end 612-2 of the bottle 612 and extends from an exterior of the bottle 612 to an interior thereof. The second interconnect component 618 is preferably coupled to an interior of the first interconnect component 620. The hydrophobic membrane may be coupled to a rim of the second interconnect component 618, and be configured to receive the chlorine dioxide gas therethrough and produce a cleaning solution with the liquid therein.

In one example, the first interconnect component 620 extends through the locking member 624, which may be a ring-shaped band. The locking member 624 may be located in the interior of the bottle 612, as shown in FIG. 14. The first interconnect component 620 may include a base portion 620-1 and a protrusion 620-2. The base portion 620-1 may be located on an exterior of the bottle 612, as shown in FIG. 14. The protrusion 620-2 preferably extends from the base portion 620-1 into the interior of the bottle 612, and is located internal with respect to the locking member 624 in a press-fit manner in order to lock the first interconnect member 620 on the bottle 612.

It will also be appreciated that the second interconnect member 618 is threadably coupled to an interior of the first interconnect member 620. Additionally, as shown in FIG. 15, the second interconnect component 618 has a guard portion (e.g., cross-shaped guard portion 618-1) at a bottom side thereof in order to: a) minimize access to the hydrophobic membrane 616 (e.g., a user cannot reach through the bottom to interact with the hydrophobic membrane 616, and b) allow the second interconnect member 618 to be threadably coupled to the first interconnect member 620.

Figure 16A:
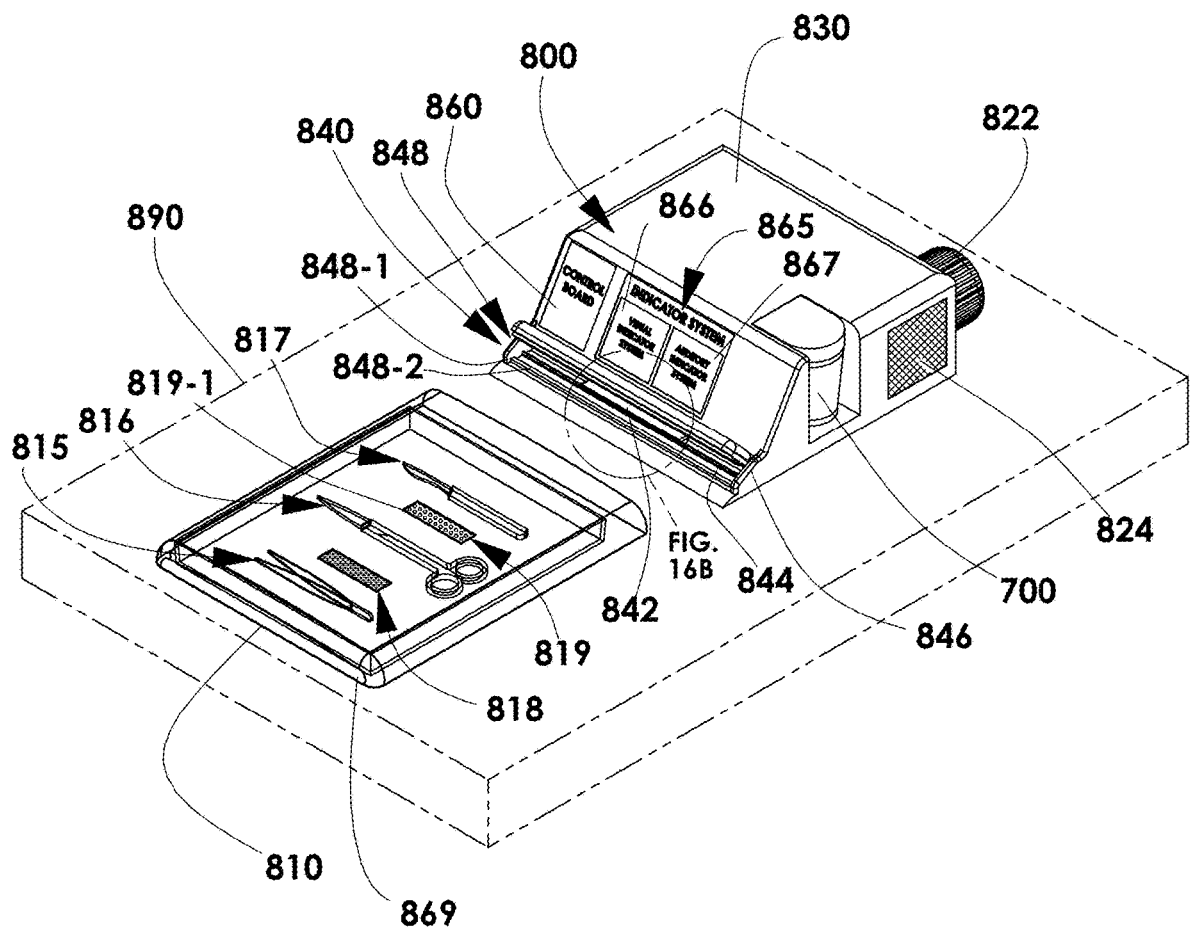
FIG. 16A depicts a chlorine dioxide gas generating system for sterilizing equipment.

FIG. 16A shows an isometric view of a chlorine dioxide gas generating system 800, shown as employed on a support structure 890 and for use with sterilizing equipment (e.g., without limitation, surgical equipment 815, 816, 817) in a chamber (e.g., expandable bag 810). In one example, the system 800 is configured similar to the system 200 (FIG. 4), and like components represent like features. For example, the system 800 preferably includes a chlorine dioxide gas generating device 700, which is configured similar to and functions similar to the chlorine dioxide gas generating devices 100, 400, 500 (e.g., is a portable and removable device with respect to an associated chlorine dioxide gas generating system, and generates chlorine dioxide gas via electrolysis from a reagent solution responsive to an electric current being passed into an anode and a cathode of the device 700). Additionally, the system 800 also preferably includes a vacuum pump 822 fluidly coupled (e.g., connected together via one or more conduits such that a gaseous fluid can flow therebetween) to the device 700, a filter (e.g., carbon filter 824) fluidly coupled to the vacuum pump 822, and a main housing 830 configured to be mechanically coupled to the device 700, the vacuum pump 822, and the filter 824.

Figure 16B:
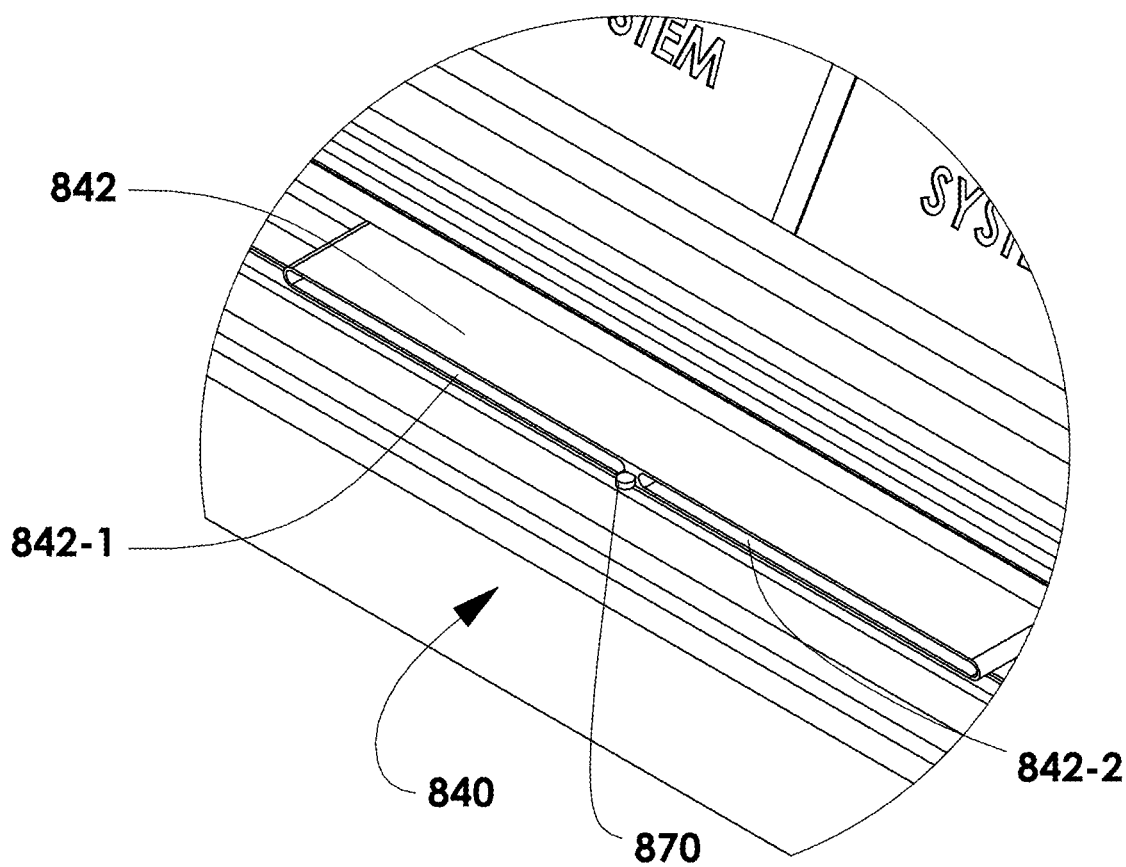
FIG. 16B depicts an enlarged view of a portion of FIG. 16A.

Continuing to refer to FIG. 16A, and also to FIG. 16B, the system 800 preferably also includes a port assembly 840. In one example, the port assembly 840 includes a port member (e.g., nozzle 842) coupled to the main housing 830 and fluidly coupled to the vacuum pump 822. It will be appreciated that by being a nozzle 842, the port member advantageously allows the chamber to be in the form of the expandable bag 810, one approved by the Food and Drug Administration for containing surgical equipment and made of a multi-surface material that is intended for sterilization.

Using the nozzle 842 allows for use of the expandable bag 810 because it provides a controlled and directed flow of chlorine dioxide gas into the expandable bag 810. This ensures that the chlorine dioxide gas is delivered efficiently and accurately, minimizing spillage and waste. Additionally, the shape of the nozzle 842 allows for an external seal to apply pressure on the opening of the expandable bag 810, thereby generating a temporary seal around the nozzle 842. This temporary seal facilitates the gas exchange, ensuring quality assurance and accuracy in the process. Moreover, this setup allows the expandable bag 810 to remain smooth rather than embossed. The protruding nozzle 842 eliminates the need for embossed ridges to facilitate the transfer of chlorine dioxide gas in and out of the expandable bag 810, further enhancing the efficiency and effectiveness of the process. Additionally, as will be discussed below, the nozzle 842 is configured to be maintained in an interior of the expandable bag 810 in order to allow the surgical equipment 815, 816, 817 in the expandable bag 810 to be sterilized by chlorine dioxide gas generated by the device 700.

Figure 18:
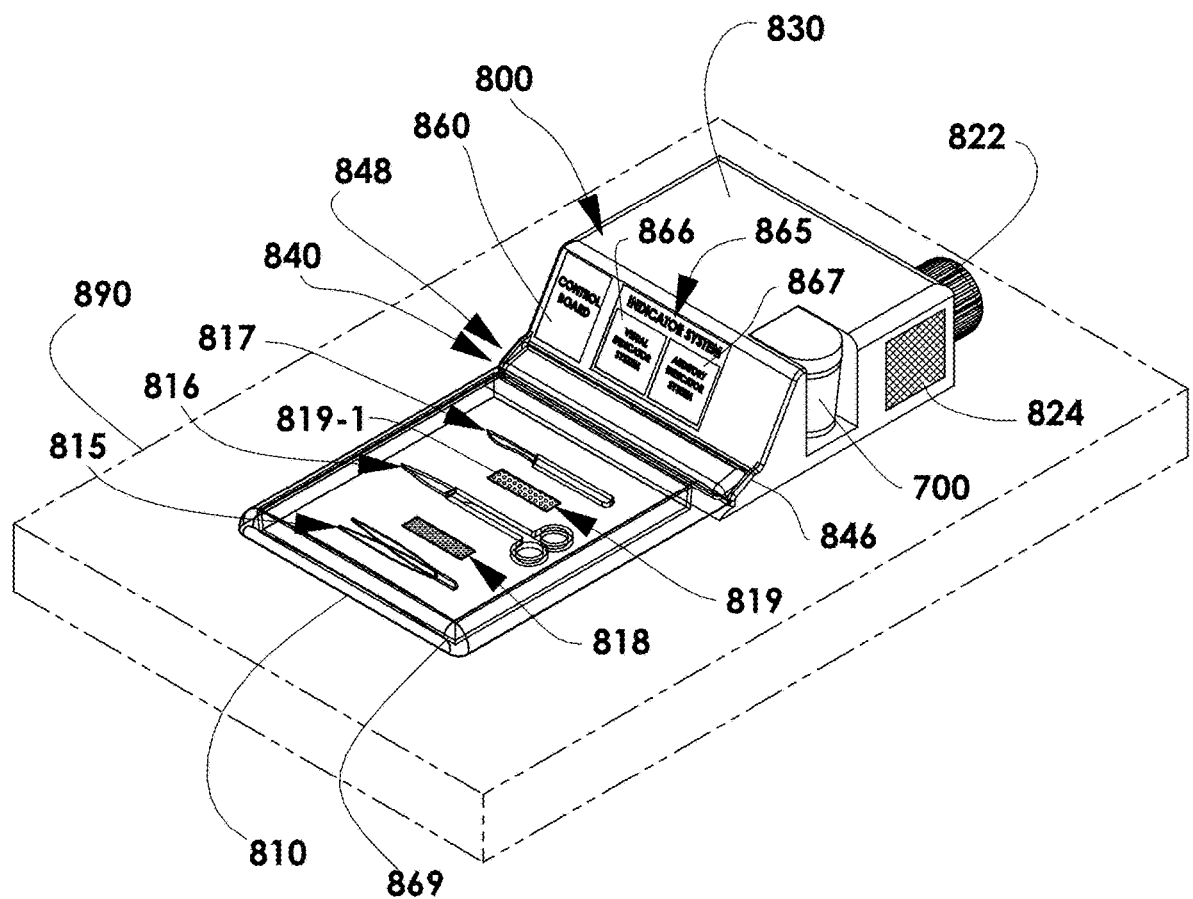
Figure 19:
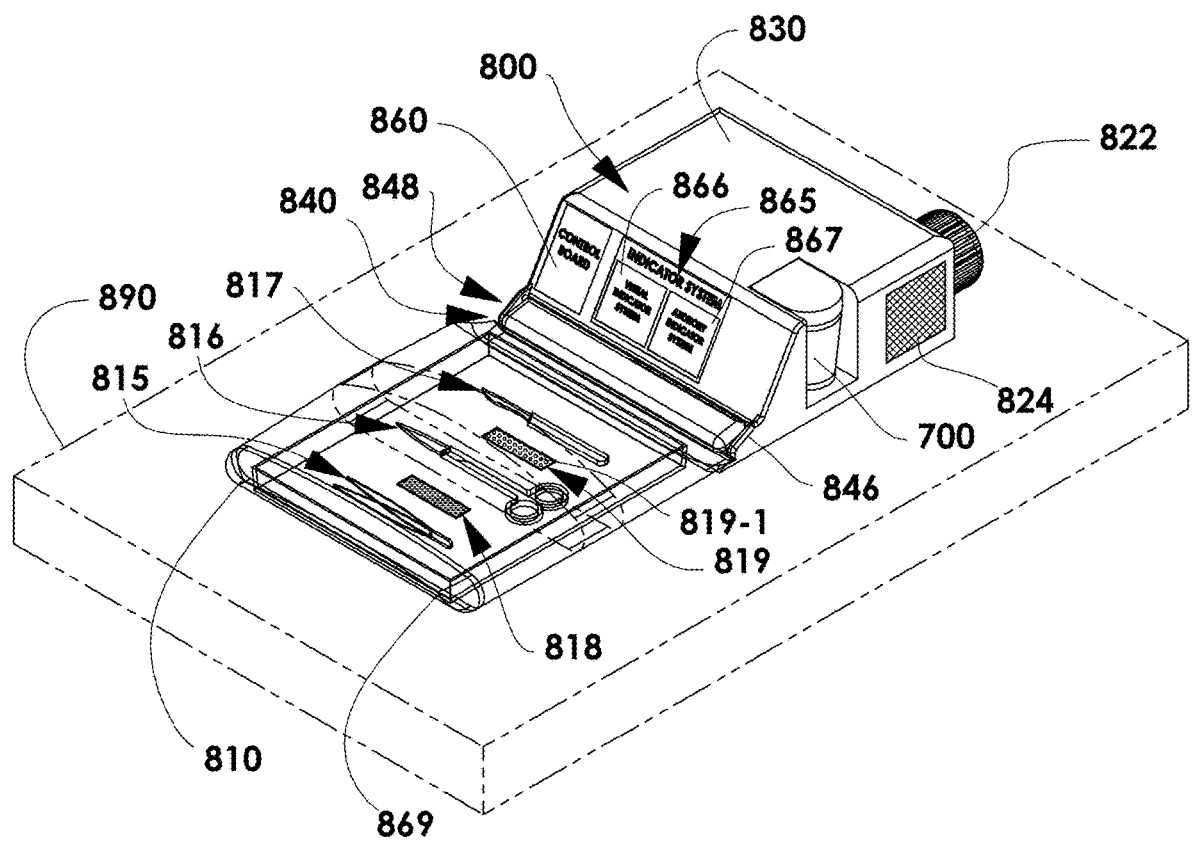

In order to perform this function, the port assembly 840 preferably also includes a clamping apparatus 844 coupled to the nozzle 842 and configured to move between an unclamped position (FIG. 17) corresponding to the nozzle 842 not being maintained in the interior of the expandable bag 810, and a clamped position (FIGS. 18-20) corresponding to the nozzle 842 being maintained in the interior of the expandable bag 810. The clamping apparatus 844 can thus be seen as clamping a distal end of the expandable 810 that defines an opening so that a sealed chamber is provided therein. In other words, the clamping apparatus 844 allows the expandable bag 810 to be vacuum sealed.

In this manner, after the expandable bag 810 has been manually moved proximate the system 800 by an individual, and clamped to a closed state by the clamping apparatus 844, the vacuum pump 822 is configured to pump the chlorine dioxide gas from device 700 into the expandable bag 810 through the nozzle 842 in order to sterilize the surgical equipment 815, 816, 817, and after a predetermined period of time, pull a gas other than the chlorine dioxide gas, such as air, into and out of the expandable bag 810 at least one time through the nozzle 842 in order to remove humidity from the expandable bag 810 and cause the chlorine dioxide gas to be drawn out of the expandable bag 810 through the nozzle 842. It will be appreciated that this step advantageously allows the chlorine dioxide gas to be removed at the same time as the other gas (e.g., air) is introduced into the expandable bag 810, which provides for desirable aeration.

Moreover, the vacuum pump 822 is also configured to draw the chlorine dioxide gas out of the expandable bag 810 and through the filter 824 in order to prevent the chlorine dioxide gas from exiting to an environment outside of the system 800. Additionally, after aerating the expandable bag 810, a desirable next step may include drawing a vacuum within the expandable bag 810 such that all gases are removed therefrom. This step is preferably performed before final sealing of the expandable bag 810.

It will be appreciated that each of these actions by the vacuum pump 822 are configured to be performed when the clamping apparatus 844 is in the clamped position. See FIG. 19, for example, which depicts chlorine dioxide gas from the device 700 being pumped into the expandable bag 810 via the fluid connection (e.g., a conduit such as a pipe) between the vacuum pump 822, the device 700, and the nozzle 842. See also FIGS. 20 and 21, for example, which depict the expandable bag 810 in an evacuated state, such as with the chlorine dioxide gas having been drawn out of the bag and air having been cycled in and out at least one time.

Figure 20:
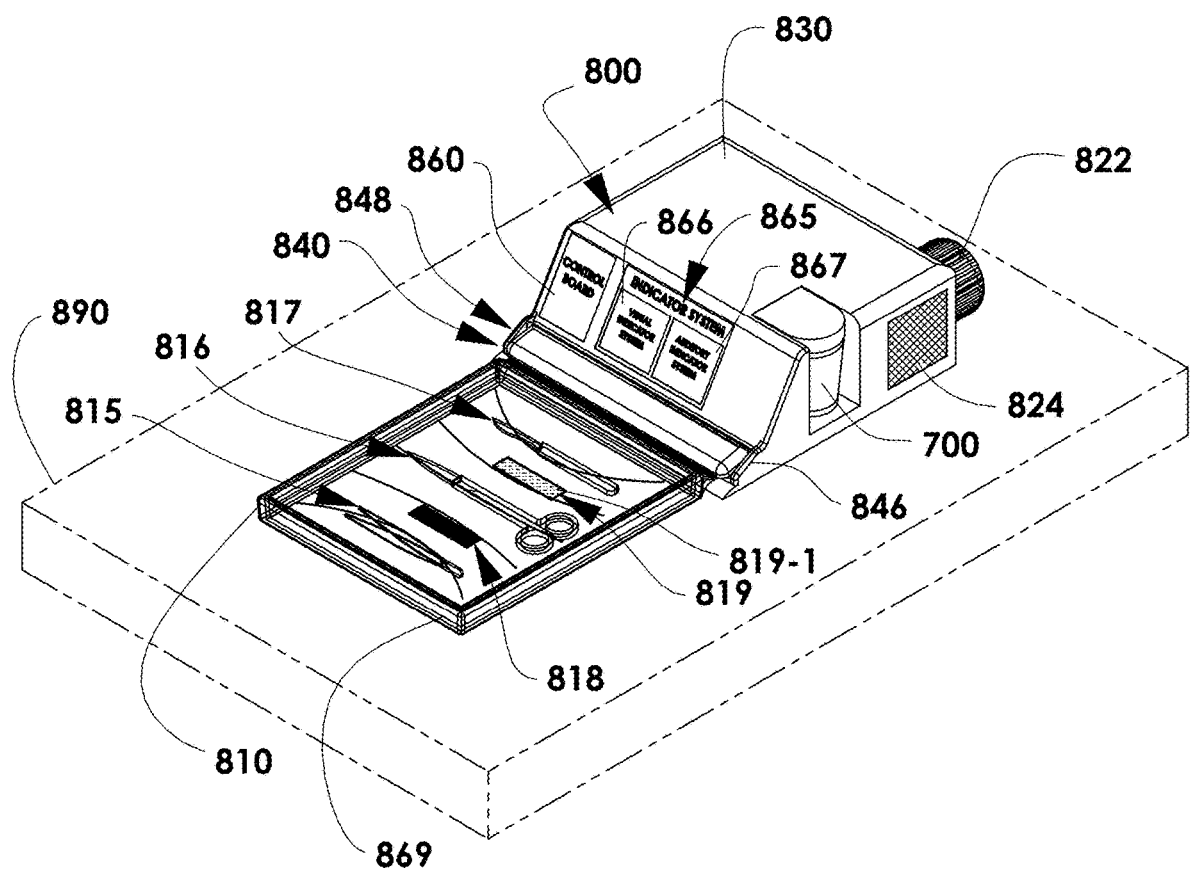
Figure 21:
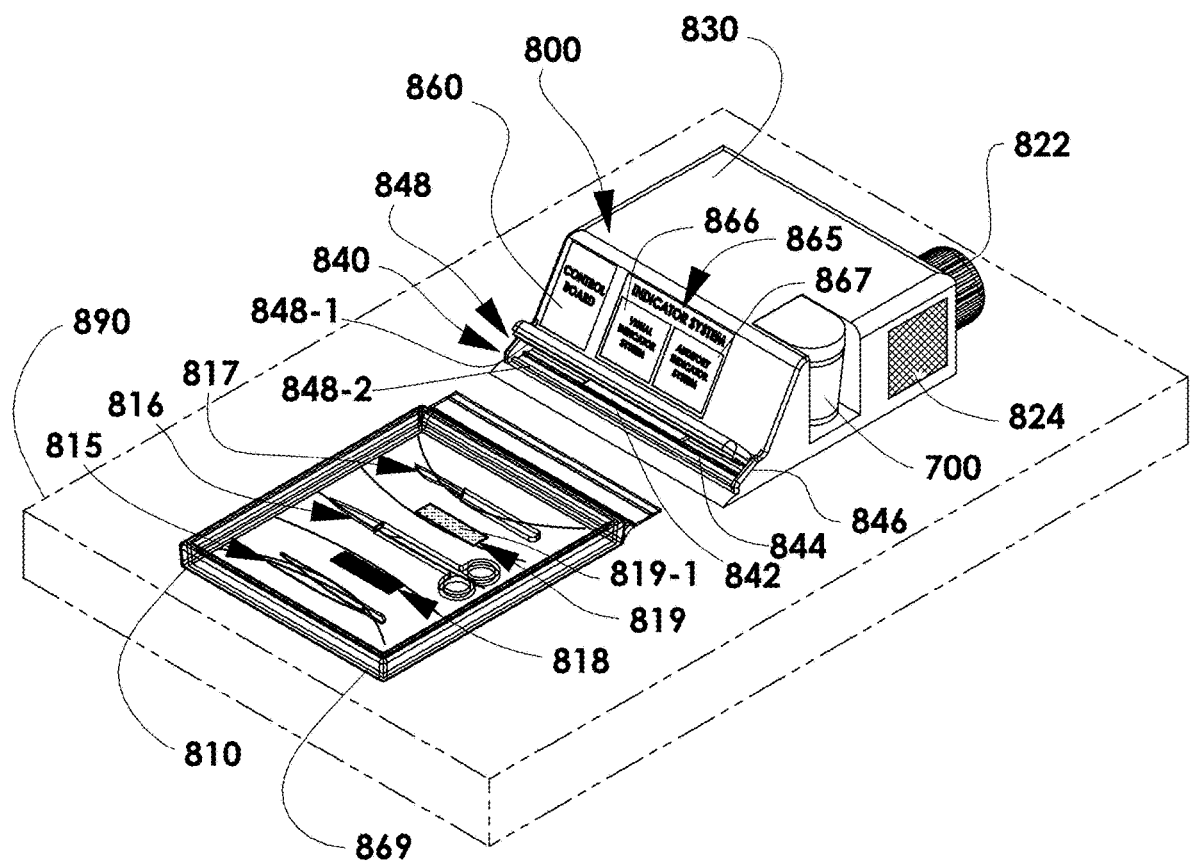

Continuing to refer to FIGS. 20 and 21, it will also be appreciated that the port assembly 840 preferably further includes a base 846 (e.g., formed as part of the main housing 830 or as a separate structure coupled to the main housing 830) and a sealing apparatus 848, with the clamping apparatus 844 and the sealing apparatus 848 each coupled to the base 846. In one example, after the gas (e.g., air) other than the chlorine dioxide gas has been pulled into and out of the expandable bag 810 at least one time, the sealing apparatus 848 is configured to move from an unsealed position corresponding to the expandable bag 810 being in an open state to a sealed position corresponding to the expandable bag 810 being in a sealed state. As shown, the sealing apparatus 848 preferably includes a first heat sealing member 848-1 and a second heat sealing member 848-2 configured to move toward the first heat sealing member 848-1 when the sealing apparatus 848 moves from the unsealed position toward the sealed position. The first and second heat sealing members 848-1, 848-2 may optionally be thermally conductive and insulative members (e.g., these members may transfer heat from the internal wiring to the sealing mechanism while losing relatively little energy). For example, the members 848-1, 848-2 may include a heating element (e.g., nichrome wire or resistance wire) for generating the heat, a seal bar for holding the heating element, a Teflon tape material covering the heating element to prevent sticking, a cushion member under the seal bar to ensure even pressure during sealing, a thermostat, and a metallic and glass fuse to protect against electrical overload. Accordingly, once the heat seal has been made to the expandable bag 810 by the sealing apparatus 848, the expandable bag 810, with the sterilized surgical equipment 815, 816, 817 located therein, is suitable for delivery to an end user, such as a physician. This is depicted in FIG. 21.

As shown in FIGS. 16A-21, the system 800 preferably further includes a control board 860 (shown in simplified form) configured to cause the electric current to be passed into the anode and the cathode of the device 700. Further, the number of times that the gas (e.g., air) other than the chlorine dioxide gas is pumped into and out of the expandable bag 810 may be a plurality of times determined by an algorithm employed by the control board 860 and based on at least one of a heat level associated with the expandable bag 810, an ultraviolet light level associated with the expandable bag 810, and an aeration level associated with the expandable bag 810. Furthermore, the system 800 also preferably includes an indicator system 865 electrically connected to the control board 860 and configured to indicate a seal status between the expandable bag 810 and the nozzle 842.

The system 800 operates effectively because its first action is to pull a complete vacuum on the expandable bag 810. If the machine fails to achieve this vacuum, internal pressure sensors and software associated with the control board 860 will detect the issue as a failed seal and halt the process. Only when the expandable bag 810 reaches a full vacuum will the software recognize it as a secure and tight seal. Any leakage will be identified as a failure, causing the system 800 to reject the cycle and prevent it from continuing. This status is then communicated through the indicator system 865, which may include at least one of a visual indicator system 866 (e.g., a blinking light) and an auditory indicator system 867 (e.g., an audible tone). Accordingly, if a secure seal is achieved, the visual indicator system 866 will preferably display a steady or blinking light, and the auditory indicator system 867 will preferably emit a confirmation tone. Conversely, if a seal failure is detected, the visual indicator system 866 will preferably flash a warning light, and the auditory indicator system 867 will preferably sound an alert tone, ensuring immediate awareness and prompt corrective action.

In one additional example, the system 800 may also include a sensor (e.g., photospectrometry sensor 870, shown more clearly in FIG. 16B) coupled to the nozzle 842, or another region of the system 800, and preferably electrically connected to the control board 860 in order to monitor a concentration of the chlorine dioxide gas in the expandable bag 810. This may be useful for a number of reasons. For example, sterilizing the surgical equipment 815, 816, 817 may involve immersing the surgical equipment 815, 816, 817 in the chlorine dioxide gas for a predetermined period of time at a predetermined concentration. By employing the sensor 870, a specific concentration can be determined by the system 800, which advantageously allows the surgical equipment 815, 816, 817 to be sterilized with greater precision. In one example, this may result in the chlorine dioxide gas being efficiently used to sterilize, and not wasted in an excessive over-use situation.

Accordingly, it will be appreciated that an example method of sterilizing the surgical equipment 815, 816, 817 in the expandable bag 810 using the system 800 includes the steps of sealing the expandable bag 810 to the nozzle 842, drawing a full vacuum in the expandable bag 810 such that all gases are substantially evacuated therefrom, generating the chlorine dioxide gas out of the solution in the device 700 via electrolysis responsive to an electric current being passed into the anode and the cathode (not shown in FIGS. 16A-21, but see anode 13 and cathode 14 in FIG. 1), pumping the chlorine dioxide gas from the device 700 into the expandable bag 810 with the vacuum pump 822 such that the chlorine dioxide gas exits the housing of the device 700 through the hydrophobic membrane of the device 700 while fluids are prevented from flowing therethrough, after a predetermined period of time, pulling a gas other than the chlorine dioxide gas into and out of the expandable bag 810 at least one time with the vacuum pump 822 in order to remove humidity from the expandable bag 810 and cause the chlorine dioxide gas to be drawn out of the expandable bag 810, and vacuum sealing, which may include heat sealing, the expandable bag 810. Accordingly, it will be appreciated that pumping may include expanding the expandable bag 810 with the chlorine dioxide gas.

Additionally, as discussed above, determining a concentration of the chlorine dioxide gas in the expandable bag 810 with the sensor 870 allows for efficiency. Thus, the pumping step may include adjusting a rate of flow of the chlorine dioxide gas with the vacuum pump 822 in order to reach a predetermined concentration of the chlorine dioxide gas in the expandable bag 810. Moreover, the example nozzle 842 may have an example first passage 842-1 and an example second passage 842-2 separate from the first passage 842. Providing the nozzle 842 structured as such advantageously allows the pumping step to include cycling the chlorine dioxide gas into the expandable bag 810 through the first passage 842-1, and out of the expandable bag 810 through the second passage 842-2, in order to reach a predetermined concentration of the chlorine dioxide gas in the expandable bag 810. In this manner, the expandable bag 810 can be said to be in a positive pressure state throughout the sterilizing process, wherein after starting the process in a full vacuum state and initially introducing the chlorine dioxide gas, cycling the chlorine dioxide gas into and out of the chamber causes a positive pressure state therein.

As mentioned, the cycling can continue until a predetermined concentration of chlorine dioxide gas is reached in the expandable bag 810. During this time, the vacuum pump 822 may be configured with a valve system (not shown), optionally controlled via solenoids electrically connected to the control board 860, to maintain a predetermined desired pressure within the expandable bag 810 (e.g., to make sure there is no over pressure or under pressure in the expandable bag 810).

In this manner, the method can be understood as first pulling a vacuum in the expandable bag 810, filling the expandable bag 810 with fresh air by pulling the fresh air through the device 700 in order to introduce a first burst of the chlorine dioxide gas into the expandable bag 810 while it is in full vacuum. This process preferably continues until the expandable bag 810 is filled and is holding pressure. Subsequently, once a predetermined pressure has been reached in the expandable bag 810, the system 800 switches from constantly delivering the chlorine dioxide gas into the expandable bag 810, to cycling the chlorine dioxide gas to the device 700 and back to the expandable bag 810, until a desired ppmv (parts per million in volume) is reached. The system 800 may stop once the predetermined concentration is reached for a specified time to reach sterilization, then aerate, and then vacuum seal, as discussed above.

The method may also further include maintaining the predetermined concentration for a predetermined period of time, which may be less than 20 minutes. In one example, having a period of time be less than 20 minutes is considerably less than known methods of sterilizing surgical equipment, which may be up to several hours depending on the method used. For instance, ethylene oxide sterilization can take up to 12 hours due to the need for extensive aeration to remove toxic residues, while steam sterilization, though faster, still requires significant time for heating and cooling cycles. In contrast, the system 800 and associated method not only reduces the overall time required but also ensures thorough internal aeration, thereby eliminating the need for extended aeration periods and enhancing operational efficiency.

In other words, this shorter time frame is preferably due to the efficient internal aeration process of the system 800, which eliminates the need for extended aeration periods required by larger chlorine dioxide sterilizers. Additionally, compared to ethylene oxide sterilizers that require lengthy aeration to remove toxic residues, steam sterilizers that need significant time for heating and cooling cycles, and hydrogen peroxide sterilizers that involve complex cycles, the system 800 offers a faster, safer, and more efficient sterilization solution.

Furthermore, although the disclosed system and method have been discussed in association with pulling the chlorine dioxide gas into the filter 824 in order to prevent the chlorine dioxide gas from being directed to an outside environment (e.g., a self-contained assembly), it will also be appreciated that the method may further include, after pulling the gas other than the chlorine dioxide gas into and out of the expandable bag 810, directing the chlorine dioxide gas and the gas other than the chlorine dioxide gas into a conduit for delivery to an outside environment. In such an example, instead of using the filter 824 to capture and neutralize the chlorine dioxide gas, the system 800 can utilize a controlled conduit system to safely direct the gases outside. This approach may eliminate the need for the filter 824, thereby reducing maintenance requirements and potential filter replacement costs. Additionally, it preferably ensures that the sterilization process remains efficient and environmentally safe by properly managing the release of gases.

Figure 17:
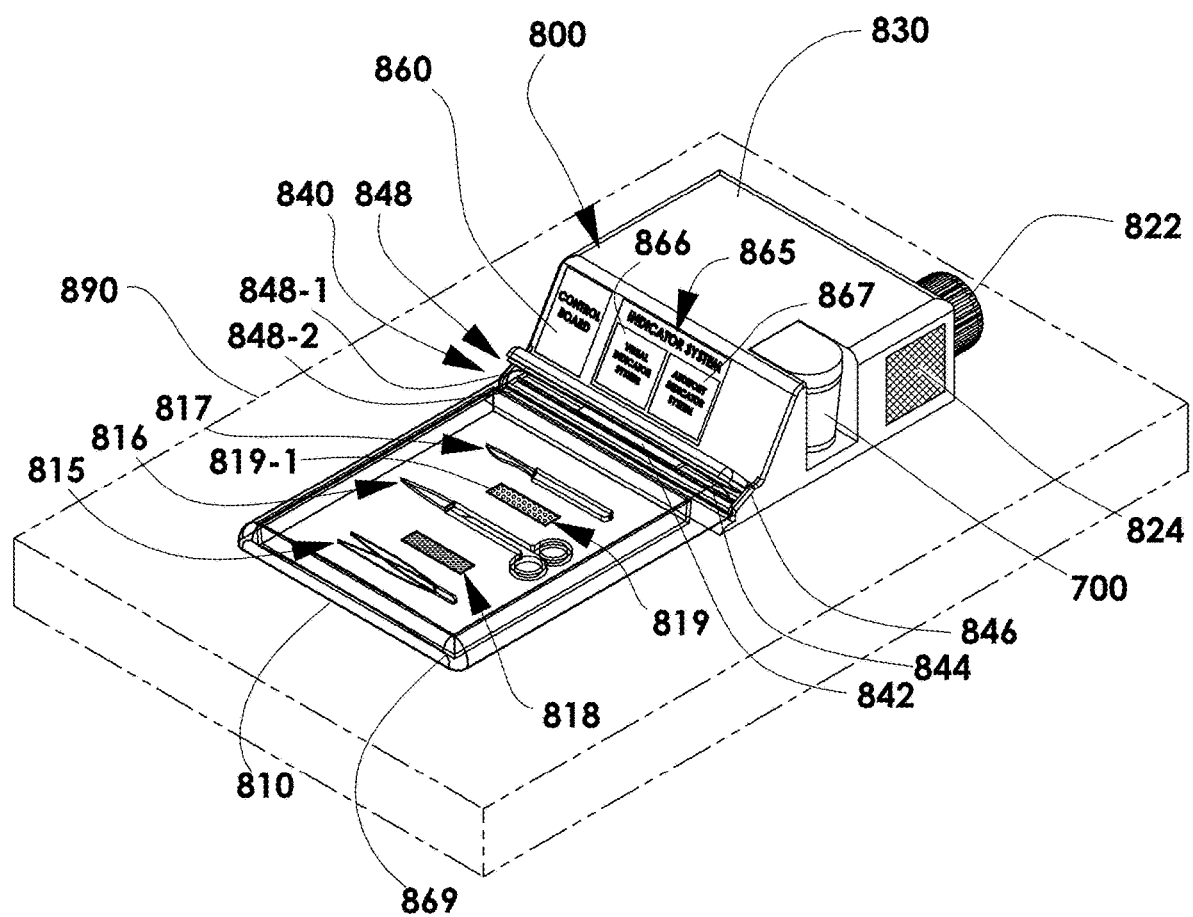
FIGS. 17-21 depict the system of FIG. 16A with a clamping apparatus in an unclamped position, with a clamping a clamped position, with an expandable bag in an expanded state, with an expandable bag in an evacuated state, and with an expandable bag having been heat sealed by a sealing apparatus of the system, respectively.

Moreover, in accordance with the disclosed concept, the method may also include disposing at least one chlorine dioxide gas indicator strip 818, 819 in the expandable bag 810 before sealing the expandable bag 810 to the nozzle 842. As shown in FIGS. 17 and 20, the strips 818, 819 are configured to change from a first state (FIG. 17) to a second, different state (FIG. 20), responsive to engagement and/or exposure with the chlorine dioxide gas. The first strip 818 is preferably configured to change from a first color to a second, different color, responsive to engagement with the chlorine dioxide gas, and the second strip 819, which may be a biological strip, preferably contains a plurality of spores 819-1 each configured to change from a live state to a dead state, responsive to engagement with the chlorine dioxide gas. As a result, a physician attempting to unseal the expandable bag 810 and use the surgical equipment 815, 816, 817 will know ahead of time whether the surgical equipment 815, 816, 817 has been properly sanitized.

In one example, the method may further include a step of wrapping the surgical equipment 815, 816, 817 in paper 869 (shown transparently in FIGS. 16A-21 in simplified form for ease of illustration), and disposing the surgical equipment 815, 816, 817 within the expandable bag 810 before sealing the expandable bag 810 to the nozzle 842. In practice, the paper 869, which is a type of surgical cloth, serves several important functions. The paper 869 is preferably used to wrap surgical tools and trays in order to maintain their sterility until they are needed for suturing and surgery. The paper 869 also acts as a barrier to protect the surgical equipment 815, 816, 817 from contamination during storage and handling. Additionally, the paper 869 allows for the penetration of the sterilant, such as chlorine dioxide gas, ensuring that the sterilization process is effective. By using the paper 869, the method ensures that the surgical equipment remains sterile and ready for use when needed, providing an extra layer of protection and assurance for healthcare professionals.

Moreover, during surgery, the paper 869 is crucial as it maintains the sterility of the surgical equipment 869 until they are unwrapped and used. The paper 869 also helps in organizing the surgical equipment 815, 816, 817 and trays, making it easier for the surgical team to access the necessary instruments quickly and efficiently. The use of this paper 869 in surgery ensures that the instruments remain uncontaminated right up until the moment they are needed, thereby reducing the risk of infection and improving patient safety. Additionally, this paper 869 can be used as protective drapes during surgery, providing a sterile barrier between the surgical field and the surrounding environment. It is also utilized for other surgical needs, such as covering patients and equipment, to maintain a sterile environment throughout the procedure.

FIGS. 22A-22F show various views of another port assembly 940 that may be used with the system 800, and shown as employed with another chamber (e.g., expandable bag 910, shown in phantom line drawing). As shown, the port assembly 940 includes a port member (e.g., nozzle 942), a clamping apparatus 944, a base 946, and a sealing apparatus 948. The clamping apparatus 944 and the sealing apparatus 948 are each preferably coupled to the base 946. In one example, the clamping apparatus 944 includes a first elongated member 944-1 and a second elongated member 944-2 configured to move toward the first elongated member 944-1 and clamp the nozzle 942 therebetween when the clamping apparatus 944 moves from the unclamped position toward the clamped position. The first and second members 944-1, 944-2 may be made of a suitable monomeric, polymeric, or mixture thereof material, such as silicone.

Figure 22A:
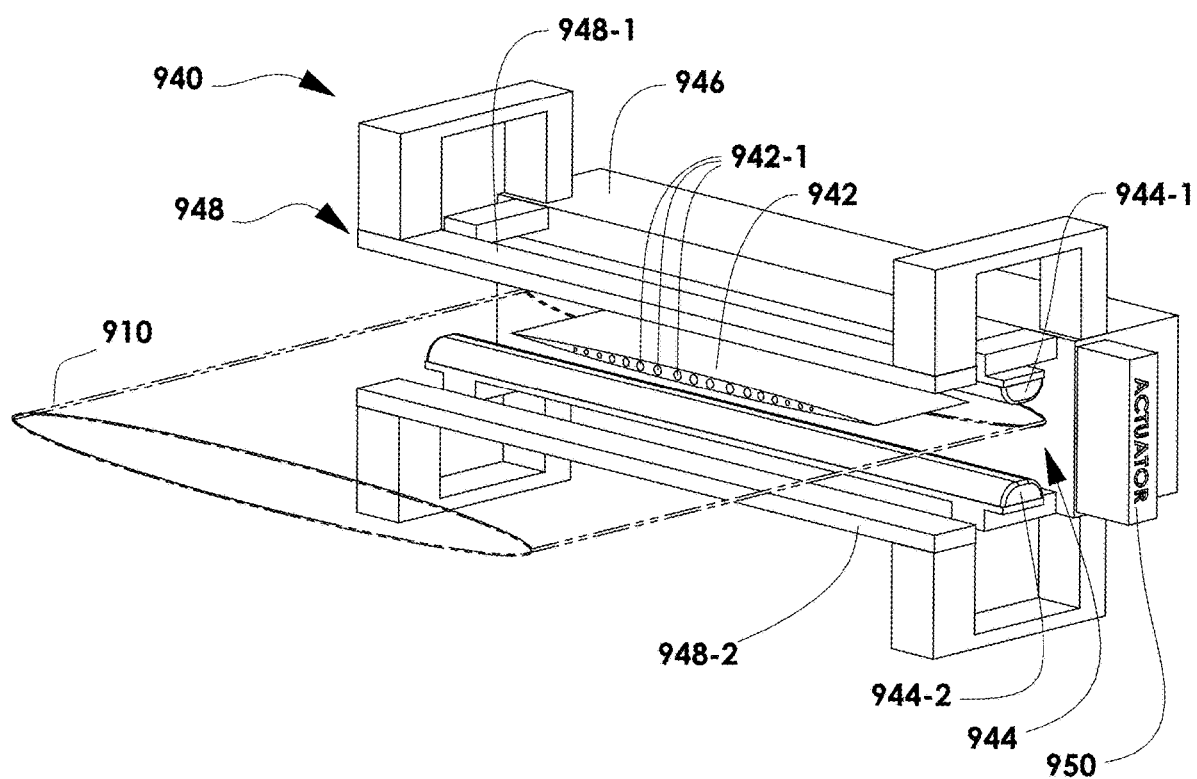
FIGS. 22A-22F show a port assembly for use in the system of FIG. 16A, and an isometric view with a clamping apparatus in an unclamped position, a side view of the same, a front view of the same, an isometric view with the clamping apparatus in a clamped position, an isometric view with a sealing apparatus in a sealed position, and a side view of the same, respectively.
Figure 22B:
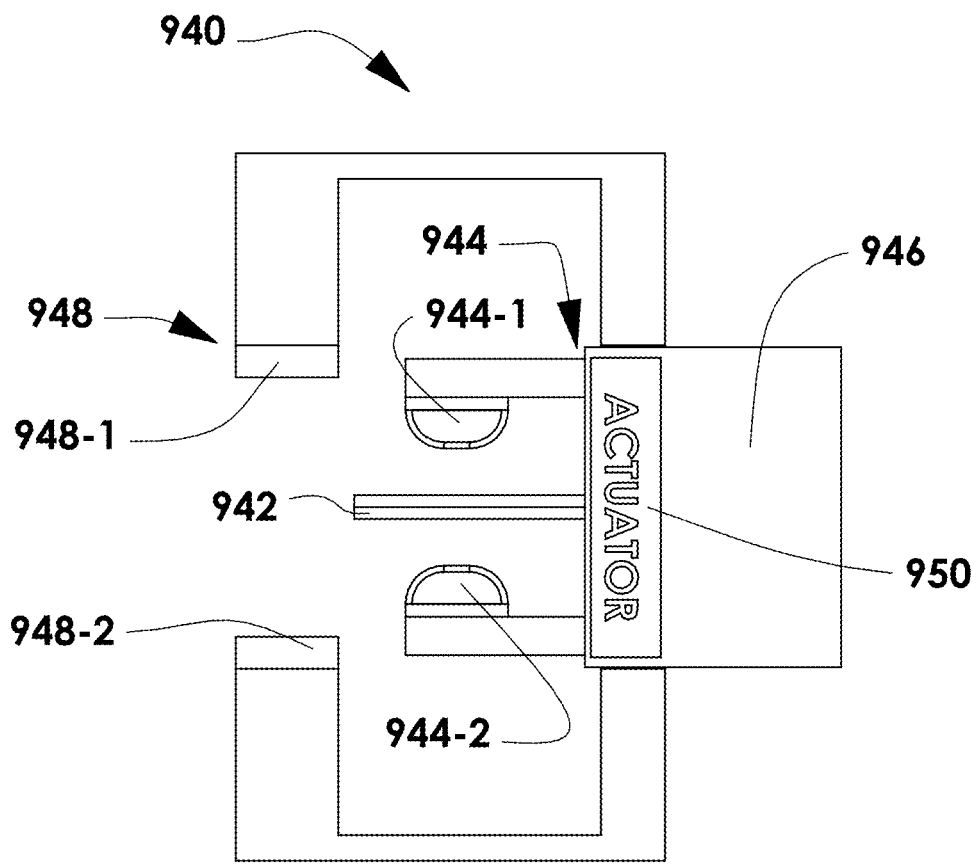
Figure 22C:
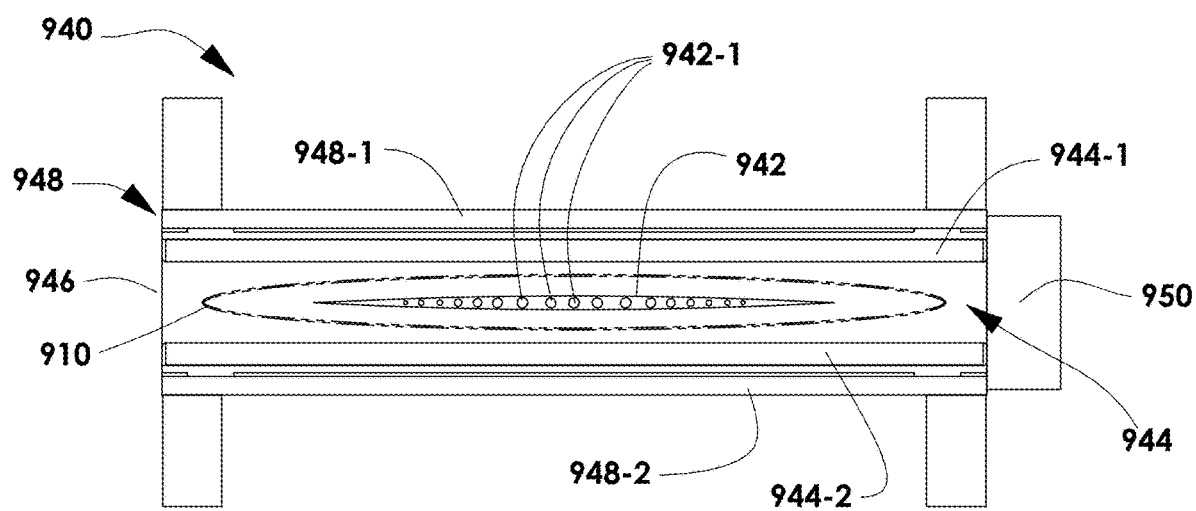
Figure 22D:
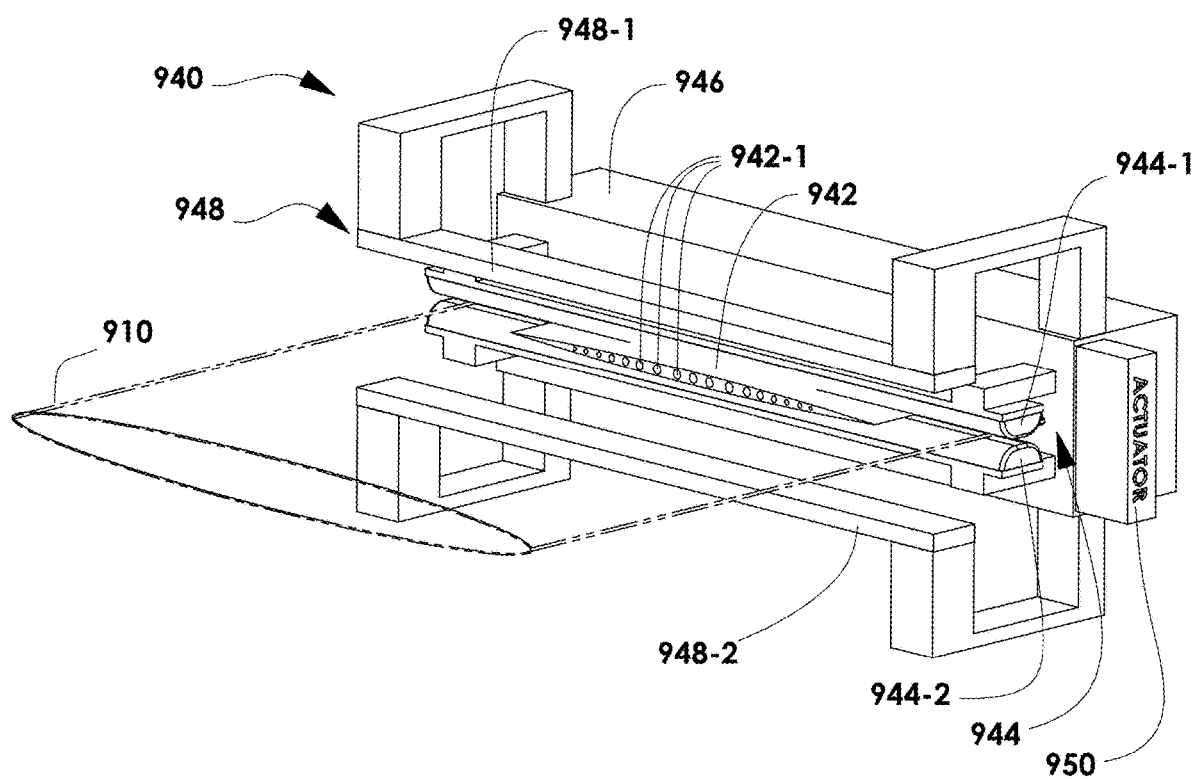
Figure 22E:
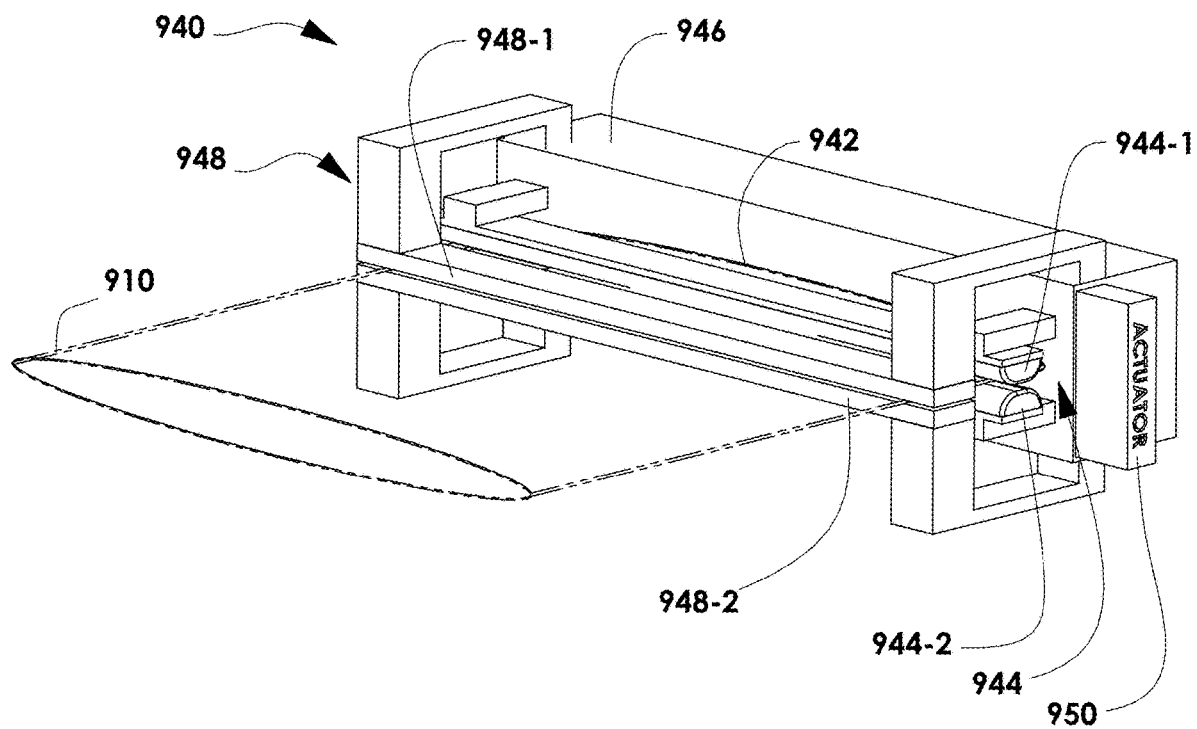
Figure 22F:
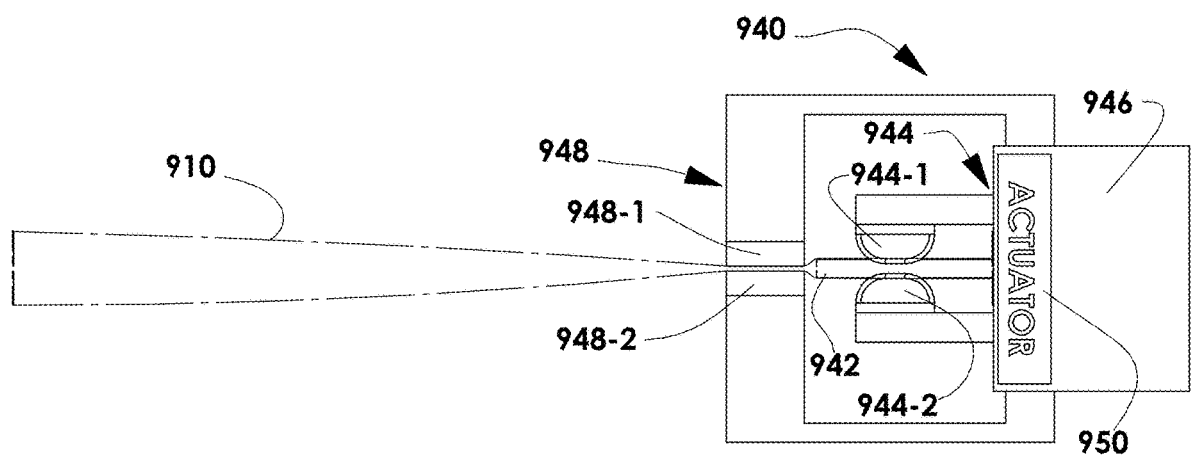

Compare, for example, FIGS. 22A-22C, which show the first and second members 944-1, 944-2 spaced from the nozzle 942 and each other (e.g., an unclamped position), with FIGS. 22D-22F, which show at least one of the first and second members 944-1, 944-2 having moved toward a position in which the first and second members 944-1, 944-2 clamp the expandable bag 910 into the nozzle 942 (e.g., a clamped position) in order to allow the chlorine dioxide gas to be pumped into and out of the expandable bag 910 without leaking to an outside environment.

Furthermore, and referring to FIGS. 22D-22F, after the gas (e.g., air) other than the chlorine dioxide gas has been pulled into and out of the expandable bag 910 (e.g., after aeration) at least one time, the sealing apparatus 948 is configured to move from an unsealed position (FIG. 22D) corresponding to the expandable bag 910 being in an open state to a sealed position corresponding to the expandable bag 910 being in a sealed state. The sealing apparatus 948 preferably includes a first heat sealing member 948-1 and a second heat sealing member 948-2 configured to move toward the first heat sealing member 948-1 when the sealing apparatus 948 moves from the unsealed position toward the sealed position. In one example, an actuator 950, which may be at least one solenoid or at least one motor, is configured to move the clamping and sealing apparatuses 944, 948 between positions. Accordingly, after the sealing apparatus 948 has moved to the sealed position (FIG. 22E), the surgical equipment (not shown in FIG. 22E, but see surgical equipment 815, 816, 817 in FIG. 16A) is vacuum sealed in the expandable bag 910.

Referring again to FIGS. 22A and 22C-22D, the nozzle 942 preferably has a plurality of through holes 942-1 in order to allow the chlorine dioxide gas and the gas other than the chlorine dioxide gas (e.g., air for aeration purposes) to be pumped into and out of the expandable bag 910 through a plurality of different fluid pathways. The through holes 942-1 may be configured as first and second passages (e.g., optionally alternative between first and second passages), similar to the passages 842-1, 842-2, discussed above, in order to allow for desired cycling of the chlorine dioxide gas into and out of the expandable bag 910. The advantages of this design include enhanced gas distribution, efficient aeration, improved sterilization efficacy, reduce cycle time, minimal residual gas, versatility, and quality control assurance. The multiple through holes 942-1 ensure that the chlorine dioxide gas is evenly distributed throughout the expandable bag 910. This uniform distribution is crucial for effective sterilization, as it ensures that all surfaces of the surgical equipment are exposed to the sterilant. Additionally, by allowing air to be pumped in and out through different pathways, the system can efficiently remove residual gases after the sterilization process. This reduces the time required for aeration, making the overall process faster and more efficient.

Further, the ability to control the flow of gases through multiple pathways allows for better penetration of the chlorine dioxide gas into hard-to-reach areas of the surgical equipment. This ensures a higher level of sterilization efficacy, reducing the risk of contamination. The efficient gas exchange facilitated by the multiple through holes helps in reducing the overall cycle time of the sterilization process. This is particularly beneficial in high-demand settings where quick turnaround of sterilized equipment is essential. The design of the nozzle 942 also helps in minimizing the amount of residual chlorine dioxide gas left in the expandable bag 910 after the sterilization process. This is important for safety and environmental reasons, as it reduces the need for extensive aeration to remove toxic residues. Moreover, the system's ability to handle different gases through multiple pathways makes it versatile and adaptable to various sterilization needs. It can be used for different types of equipment and in different settings, enhancing its utility. Finally, having multiple of the through holes 942-1 for gas transfer reduces the risk of blockage, ensuring consistent and reliable performance. This redundancy enhances the system's reliability and ensures that the sterilization process is not compromised due to a single point of failure. It also provides an additional layer of quality control, ensuring that the sterilization process meets the highest standards of safety and efficacy.

Figure 27:
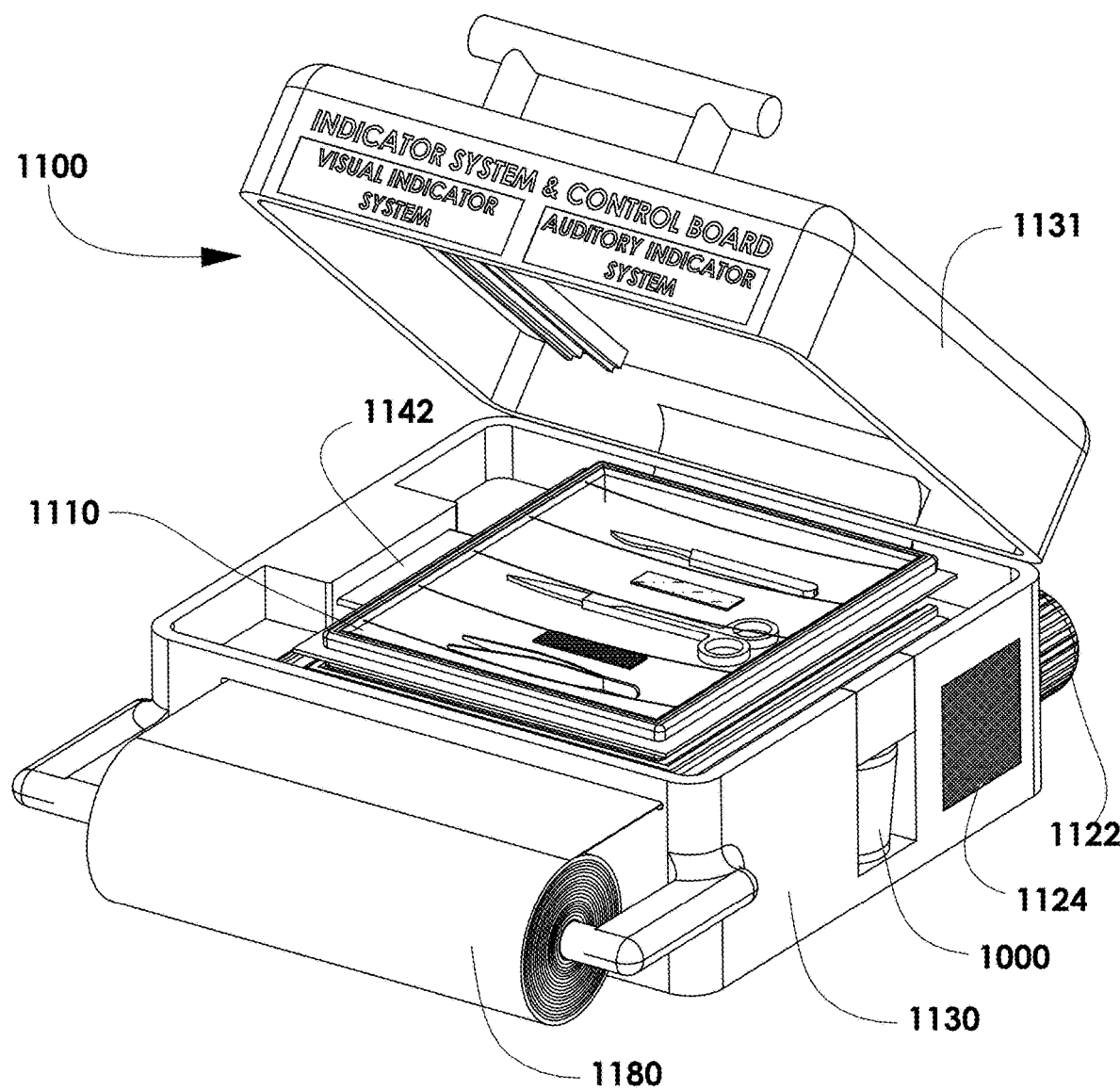

FIGS. 23-27 show another chlorine dioxide gas generating system 1100, in accordance with another non-limiting embodiment of the disclosed concept. The system 1100 is configured similar to the system 800 (FIG. 16A), and like numbers represent like features. Accordingly, the system 1100 has a chlorine dioxide gas generating device 1000, a vacuum pump 1122, a filter 1124, a main housing 1130 and other similar components, shown but not labeled. In one example, the system 1100 further includes a directing member (e.g., lid 1131) movably associated, optionally coupled, with the main housing 1130, and a roll of material 1180 coupled to the main housing 1130. The main housing 1130 is coupled to the device 700 and the vacuum pump 1122, and the roll of material 1180 is configured to be directed by the lid 1131 in order to form the expandable bag 1110 (FIG. 27).

More specifically, in one example, the roll of material 1180, which may plastic, is configured to be fed into the system 1100, such as above a top portion of the main housing 1130. The material is continually fed, at which point the lid 1131, or a suitable alternative directing member such as a lever, directs the material to form two layers of the material on top of each other. Subsequently, the surgical equipment 1115, 1116, 1117 (shown on a transparent simplified rendering of surgical paper) and indicator strips 1118, 1119 are placed onto the first layer of the material, a heat seal is formed between top and bottom layers, and an expandable bag is created and configured to be used in a sterilization process via a nozzle 1142, in the same manner as depicted above with reference to FIGS. 16-21. This functionality and associated process is depicted in FIGS. 23-27.

Figure 23:
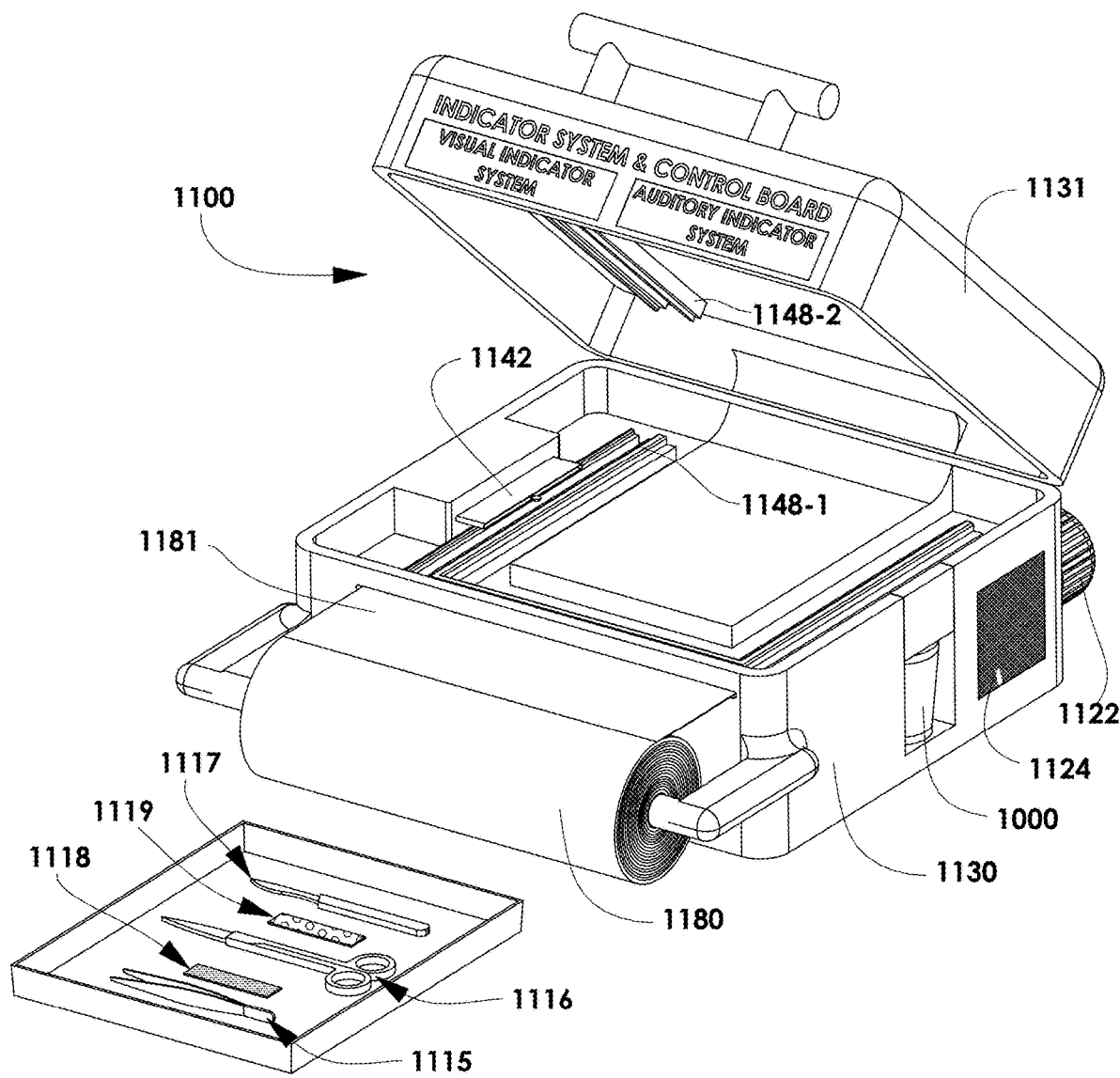
FIGS. 23-27 show various views of another chlorine dioxide gas generating system, in accordance with another non-limiting embodiment of the disclosed concept, and with a roll of material not dispensed with respect to a main housing, partially dispensed with respect to a main housing, fully dispensed with respect to a main housing and with surgical equipment disposed thereon, with a directing member moved with respect to a main housing, and with an expandable bag fully formed from the roll of material by the system, respectively.
Figure 24:
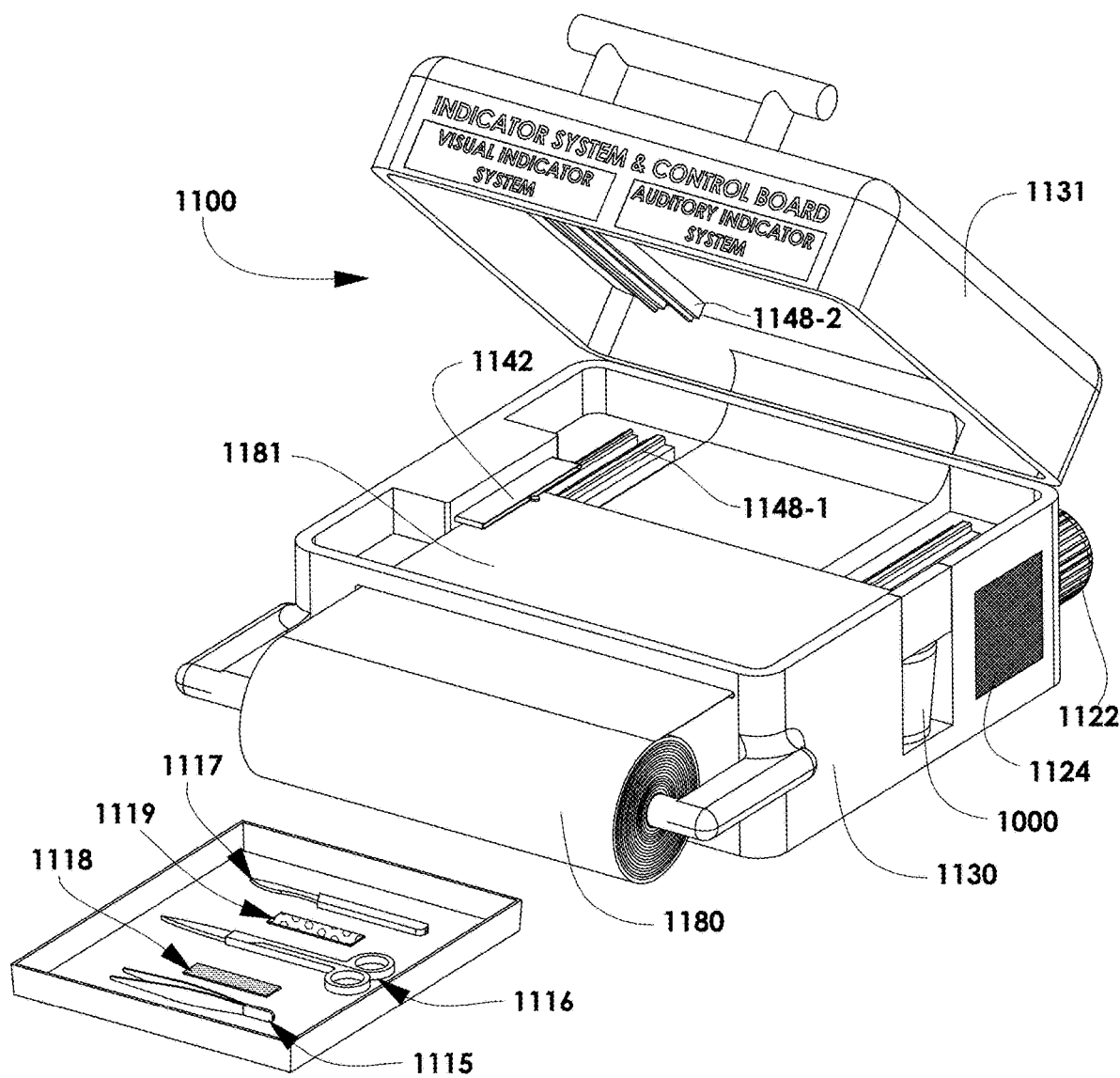
Figure 25:
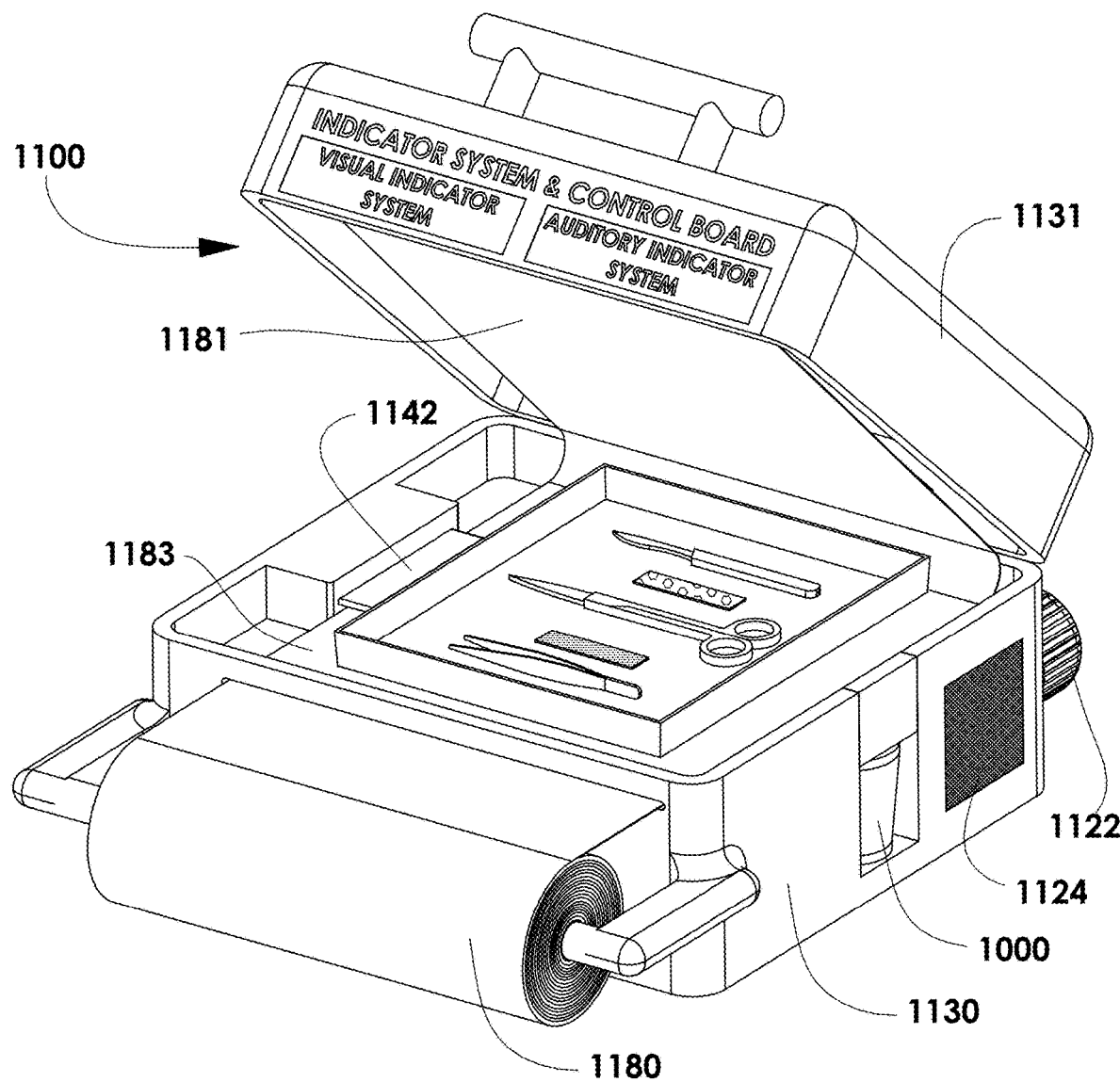
Figure 26:
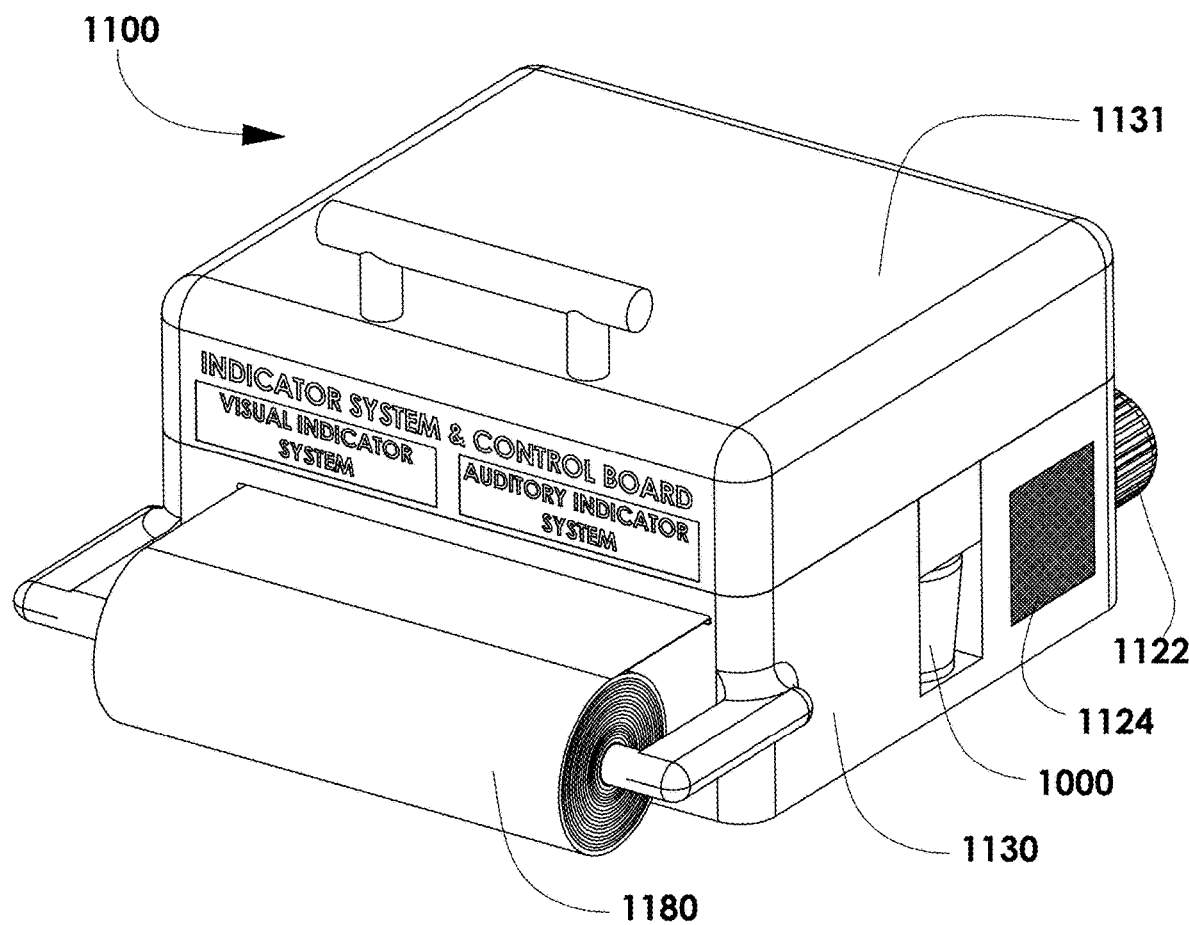

First, in FIG. 23, the lid 1131 may be opened, or in a suitable alternative arrangement, the roll of material 1180 is prepared for dispensing with respect to the main housing 1130. Subsequently, the roll of material 1180 is dispensed. See, for example, FIG. 24 in which a first portion 1181 of the roll of material 1180 is directed with respect to a top of the main housing 1130. Next, in FIG. 25, the first portion 1181 is continually directed by the lid 1131, in this non-limiting example being done so as to traverse an inner portion of the lid 1131. Additionally, as shown in this step, the surgical equipment 1115, 1116, 1117 and the strips 1118, 1119 are configured to be manually placed on a bottom layer 1181-1 of the first portion 1181 of the roll of material 1180. Once this is done, the system 1100 is ready to form the expandable bag 1110 (FIG. 27) and begin the sterilization process.

More specifically, the system 1100 preferably further includes at least one sealing apparatus (e.g., in the form of first and second U-shaped heat sealing members 1148-1, 1148-2) coupled to at least one of the main housing 1130 and the lid 1131, respectively. In one example, responsive to the first portion 1181 of the roll of material 1180 being directed by the lid 1131, the sealing apparatus is configured to seal the first portion 1181 of the roll of material 1180 to a second, different portion 1183 of the roll of material by creating a heat seal therebetween, thereby forming the chamber and enclosing the equipment therein.

In the depicted example, the U-shaped heat sealing member 1148-2 provided with the lid 1131 is configured to be moved, optionally manually moved, toward engagement with the U-shaped heat sealing member 1148-1 provided with the main housing 1130. Once this step is performed, as discussed, a chamber in the form of an expandable bag 1110 (FIG. 27) is formed, thereby allowing chlorine dioxide gas to be pumped in and reach a predetermined concentration, followed by aeration, etc. for sterilizing the surgical equipment 1115, 1116, 1117, e.g., via a nozzle 1142.

The system 1100 may also, in one example, be configured to form a second heat seal after aeration, thereby vacuum sealing the surgical equipment 1115, 1116, 1117 and the strips 1118, 1119 in the fully sealed and encapsulated expandable bag 1110. Additionally, shown but not labeled in the embodiment of FIGS. 23-27 is a clamping apparatus which functions similar to the clamping apparatus 844, 944 of FIGS. 16A-22F.

It will also be appreciated that the system 1100 may be configured for other general packaging purposes beyond sterilization, including but not limited to food packaging, pharmaceutical packaging, medical device packaging, electronic component packaging, biological sample packaging, industrial parts packaging, cosmetic packaging, and agricultural product packaging. The system 110 can be used to package perishable food items in a controlled atmosphere, extending shelf life by reducing exposure to oxygen and contaminants. Ensuring the sterility and integrity of pharmaceutical products during storage and transport by using the system 1100 advantageously creates a sterile barrier. Packaging medical devices with the system 1100 in a sterile environment desirably maintains their sterility until use, similar to its application in surgical equipment sterilization. Protecting sensitive electronic components from moisture, dust, and static by sealing them in a controlled environment is achievable with the system 1100. Safely packaging biological samples for transport and storage with the system 1100 ensures they remain uncontaminated and viable for analysis. Packaging industrial parts and tools with the system 1100 prevents corrosion and contamination during storage and transport. Ensuring the sterility and preservation of cosmetic products, particularly those that are sensitive to contamination, is achievable with the system 1100. Finally, packaging seeds, plants, and other agricultural products to protect them from pests and environmental factors is achievable with the system 1100. These additional uses highlight the versatility of the system 1100, making it a valuable tool for various industries beyond sterilization.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

Although specific embodiments of the disclosure have been described, numerous other modifications and alternative embodiments are within the scope of the disclosure. For example, any of the functionality described with respect to a particular device or component may be performed by another device or component. Further, while specific device characteristics have been described, embodiments of the disclosure may relate to numerous other device characteristics. Further, although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments may not include, certain features, elements, and/or steps. Thus, such conditional language is not generally intended to imply that features, elements, and/or steps are in any way required for one or more embodiments.

What is claimed is:

1. A chlorine dioxide gas generating system for sterilizing equipment in an expandable bag, the system comprising:
   a chlorine dioxide gas generating device comprising a housing having a cavity, an anode and a cathode each coupled to and disposed within the cavity, and a solution comprising a first amount of a first reagent and a second amount of a second reagent, the first and second amounts each disposed within the cavity and configured to generate chlorine dioxide gas out of the solution via electrolysis responsive to an electric current being passed into the anode and the cathode, wherein, as the electric current is passed into the anode and the cathode, the first and second amounts each continually decrease until the first and second amounts are about zero;

a vacuum pump fluidly coupled to the chlorine dioxide gas generating device and configured to both expand the bag and draw a vacuum within the bag;

a port assembly comprising a port member and a clamping apparatus coupled to the port member, the port member being fluidly coupled to the vacuum pump and configured to be maintained in an interior of the bag, the clamping apparatus being configured to move between an unclamped position corresponding to the port member not being maintained in the interior of the bag, and a clamped position corresponding to the port member being maintained in the interior of the bag; and a control board electrically connected to the vacuum pump and configured to control the vacuum pump for maintaining a predetermined desired pressure within the bag, wherein, when the clamping apparatus is in the clamped position, the vacuum pump is configured to pump the chlorine dioxide gas from the chlorine dioxide gas generating device into the bag through the port member in order to sterilize the equipment, and after a predetermined period of time, pull a gas other than the chlorine dioxide gas into and out of the bag at least one time through the port member in order to remove humidity from the bag and cause the chlorine dioxide gas to be drawn out of the bag through the port member.

2. The chlorine dioxide gas generating system according to claim 1, wherein the clamping apparatus comprises a first elongated member and a second elongated member configured to move toward the first elongated member and clamp the port member therebetween when the clamping apparatus moves from the unclamped position toward the clamped position.

3. The chlorine dioxide gas generating system according to claim 1, wherein the port assembly further comprises a base and a sealing apparatus, wherein the clamping apparatus and the sealing apparatus are each coupled to the base, and wherein, after the gas other than the chlorine dioxide gas has been pulled into and out of the bag at least one time, the sealing apparatus is configured to move from an unsealed position corresponding to the bag being in an open state to a sealed position corresponding to the bag being in a sealed state.

4. The chlorine dioxide gas generating system according to claim 3, wherein the sealing apparatus comprises a first heat sealing member and a second heat sealing member configured to move toward the first heat sealing member when the sealing apparatus moves from the unsealed position toward the sealed position.

5. The chlorine dioxide gas generating system according to claim 1, further comprising a main housing, a directing member movably associated with the main housing, and a roll of material coupled to the main housing, wherein the main housing is coupled to the chlorine dioxide gas generating device and the vacuum pump, and wherein the roll of material is configured to be directed by the directing member in order to form the chamber bag.

6. The chlorine dioxide gas generating system according to claim 5, further comprising at least one sealing apparatus coupled to at least one of the main housing and the directing member, wherein, responsive to a first portion of the roll of material being directed by the directing member, the at least one sealing apparatus is configured to seal the first portion of the roll of material to a second, different portion of the roll of material by creating a heat seal therebetween, thereby forming the bag and enclosing the equipment therein.

7. The chlorine dioxide gas generating system according to claim 1, wherein the port member is a nozzle.

8. The chlorine dioxide gas generating system according to claim 7, wherein the nozzle has a plurality of through holes configured as alternative first and second passages in order to allow for desired cycling of the chlorine dioxide gas into the bag through the first passages, and out of the bag through the second passages.

9. The chlorine dioxide gas generating system according to claim 1, further comprising a filter fluidly coupled to the vacuum pump, and wherein the vacuum pump is configured to draw the chlorine dioxide gas out of the bag and through the filter in order to prevent the chlorine dioxide gas from exiting to an environment outside of the chlorine dioxide gas generating system.

10. The chlorine dioxide gas generating system according to claim 9, wherein the filter is a carbon filter.

11. The chlorine dioxide gas generating system according to claim 1, wherein the control board is configured to cause the electric current to be passed into the anode and the cathode, and wherein the at least one time is a plurality of times determined by an algorithm employed by the control board and based on each of a heat level associated with the bag, an ultraviolet light level associated with the bag, and an aeration level associated with the bag.

12. The chlorine dioxide gas generating system according to claim 11, further comprising an indicator system electrically connected to the control board and configured to indicate a seal status between the bag and the port member, wherein the indicator system is at least one of a visual indicator system and an auditory indicator system.

13. The chlorine dioxide gas generating system according to claim 1 further comprising a photospectrometry sensor coupled to the port member in order to monitor a concentration of the chlorine dioxide gas in the bag.

14. The chlorine dioxide gas generating system according to claim 1, wherein the chlorine dioxide gas generating device further comprises a fluid control apparatus configured to increase a rate of release of the chlorine dioxide gas and diffuse splashing of the solution responsive to the increase in the rate of release of the chlorine dioxide gas.

15. A method of sterilizing equipment in an expandable bag using a chlorine dioxide gas generating system, the chlorine dioxide gas generating system comprising a chlorine dioxide gas generating device, a vacuum pump fluidly coupled to the chlorine dioxide gas generating device and configured to both expand the bag and draw a vacuum within the bag, a port member fluidly coupled to the vacuum pump, a clamping apparatus coupled to the port member, and a control board electrically connected to the vacuum pump, the chlorine dioxide gas generating device comprising a housing having a cavity, an anode and a cathode each coupled to and disposed within the cavity, and a solution comprising a first amount of a first reagent and a second amount of a second reagent, the first and second amounts each disposed within the cavity, the method comprising:

moving the clamping apparatus between an unclamped position corresponding to the port member not being maintained in the interior of the bag, and a clamped position corresponding to the port member being maintained in the interior of the bag, in order to seal the bag to the port member;

generating the chlorine dioxide gas out of the solution in the chlorine dioxide gas generating device via electrolysis responsive to an electric current being passed into the anode and the cathode, wherein, as the electric current is passed into the anode and the cathode, the first and second amounts each continually decrease until the first and second amounts are about zero;

pumping the chlorine dioxide gas from the chlorine dioxide gas generating device into the bag and expanding the bag with the vacuum pump when the clamping apparatus is in the clamped position, such that the chlorine dioxide gas exits the housing and enters the bag controlling the vacuum pump with the control board in order to maintain a predetermined desired pressure within the bag;

after a predetermined period of time, and when the clamping apparatus is in the clamped position, pulling a gas other than the chlorine dioxide gas into and out of the bag at least one time with the vacuum pump in order to remove humidity from the bag and cause the chlorine dioxide gas to be drawn out of the bag; and vacuum sealing the bag.

16. The method according to claim 15, further comprising disposing at least one chlorine dioxide gas indicator strip in the bag before sealing the bag to the port member, the at least one chlorine dioxide gas indicator strip configured to change from a first state to a second, different state, responsive to engagement with the chlorine dioxide gas.

17. The method according to claim 16, wherein the at least one chlorine dioxide gas indicator strip is at least one of a first strip and a second strip, wherein the first strip is configured to change from a first color to a second, different color, responsive to engagement with the chlorine dioxide gas, and wherein the second strip contains a plurality of spores each configured to change from a live state to a dead state, responsive to engagement with the chlorine dioxide gas.

18. The method according to claim 15, wherein pumping the chlorine dioxide gas from the chlorine dioxide gas generating device into the bag comprises adjusting a rate of flow of the chlorine dioxide gas with the vacuum pump in order to reach a predetermined concentration of the chlorine dioxide gas in the bag.

19. The method according to claim 18, further comprising maintaining the predetermined concentration for the predetermined period of time.

20. The method according to claim 19, wherein the predetermined period of time is less than 20 minutes.

21. The method according to claim 15, further comprising wrapping the equipment in paper, and disposing the equipment within the bag before sealing the bag to the port member.

22. The method according to claim 15, wherein vacuum sealing the bag comprises heat sealing the bag.

23. The method according to claim 15, further comprising, after pulling the gas other than the chlorine dioxide gas into and out of the bag, directing the chlorine dioxide gas and the gas other than the chlorine dioxide gas into a conduit for delivery to an outside environment.

24. The method according to claim 15, wherein the port member has a first passage and a second passage, and wherein pumping the chlorine dioxide gas comprises cycling the chlorine dioxide gas into the bag through the first passage, and out of the bag through the second passage, in order to reach a predetermined concentration of the chlorine dioxide gas in the bag.

25. A chlorine dioxide gas generating device, comprising:
a housing having a cavity, a first through hole, and a second through hole, the housing comprising a first portion proximate the first through hole, a second portion proximate the second through hole, and at least one sealing member;
an anode and a cathode each coupled to and disposed within the cavity; and
a solution comprising a first reagent and a second reagent disposed within the cavity and configured to generate chlorine dioxide gas out of the solution via electrolysis in a portable manner responsive to an electric current being passed into the anode and the cathode, the chlorine dioxide gas being configured to exit the housing via the first through hole while an additional gas enters the housing via the second through hole,
wherein the at least one sealing member is sealed to the first and second portions over the first and second through holes in order to prevent evaporation of the first and second reagents.

26. The chlorine dioxide gas generating device according to claim 25, further comprising a hydrophobic membrane coupled to the housing and configured to allow the chlorine dioxide gas to exit the housing while preventing fluids from flowing therethrough.

27. The chlorine dioxide gas generating device according to claim 25, wherein the chlorine dioxide gas is configured to be generated in a controllable, start and stop manner without additional reagents being circulated into the housing.

28. The chlorine dioxide gas generating device according to claim 25, wherein the housing contains a first amount of the first reagent and a second amount of the second reagent, wherein, as the electric current is being passed into the anode and the cathode, the first and second amounts of the first and second reagents each continually decrease until the first and second amounts are about zero, and wherein the chlorine dioxide gas is configured to be generated via a sole catalyst in the form of the electric current.

* * * * *